(12) United States Patent
Kudo et al.

(10) Patent No.: US 8,333,747 B2
(45) Date of Patent: Dec. 18, 2012

(54) ABSORPTIVE ARTICLE

(75) Inventors: Jun Kudo, Kagawa (JP); Akira Hashino, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 797 days.

(21) Appl. No.: 12/307,033

(22) PCT Filed: Jul. 5, 2007

(86) PCT No.: PCT/JP2007/063504
§ 371 (c)(1),
(2), (4) Date: Dec. 30, 2008

(87) PCT Pub. No.: WO2008/004636
PCT Pub. Date: Jan. 10, 2008

(65) Prior Publication Data
US 2009/0198204 A1    Aug. 6, 2009

(30) Foreign Application Priority Data

Jul. 5, 2006   (JP) ................................ 2006-186141

(51) Int. Cl.
*A61F 13/15* (2006.01)
*A61F 13/20* (2006.01)
(52) U.S. Cl. ........ 604/385.101; 604/385.01; 604/385.03
(58) Field of Classification Search ............ 604/385.01, 604/385.03, 385.101, 385.11, 385.16, 385.201, 604/385.24
See application file for complete search history.

(56) References Cited

U.S. PATENT DOCUMENTS

| | | | |
|---|---|---|---|
| 4,022,210 A | 5/1977 | Glassman | |
| 5,624,421 A | 4/1997 | Dabi et al. | |
| 5,947,947 A | 9/1999 | Tanzer et al. | |
| 6,231,556 B1 | 5/2001 | Osborn, III | |
| 6,395,956 B1 | 5/2002 | Glasgow et al. | |
| 6,471,682 B2 | 10/2002 | Kashiwagi | |
| 6,475,199 B1 | 11/2002 | Gann et al. | |

(Continued)

FOREIGN PATENT DOCUMENTS

| | | |
|---|---|---|
| JP | 10-286278 A | 10/1998 |
| JP | 11-104169 A | 4/1999 |
| JP | 2000-152957 A | 6/2000 |
| JP | 2001-245921 A | 9/2001 |
| JP | 2002-159534 A | 6/2002 |
| JP | 2008-023248 A | 2/2008 |

OTHER PUBLICATIONS

Certified Translation of Previously Cited Reference to Higuchi (JP 2002-159534).*
Office Action issued to U.S. Appl. No. 12/307,109, mailed Jul. 29, 2011.

*Primary Examiner* — Michele M Kidwell
(74) *Attorney, Agent, or Firm* — Lowe Hauptman Ham & Berner LLP

(57) ABSTRACT

Provided is an absorptive article having absorption elements capable of following the wearer's body of a user. This absorptive article comprises at least a generally rectangular base absorption element, a top absorption element disposed on one surface of the base absorption element at substantially lateral center of the base absorbent and along the longitudinal direction of the base absorbent, and a fixing part for fixing the base absorption element to the top absorption element so that at least one end of the top absorption element in the longitudinal direction thereof is made to be a free end. A locking part is provided on the base absorption element side contact surface of the top absorption element near the free end. The locking part is locked to the base absorption element at a position where the top absorption element is so moved as to extend along the gluteal cleft of the user.

11 Claims, 20 Drawing Sheets

U.S. PATENT DOCUMENTS

| | | |
|---|---|---|
| 6,508,795 B1 | 1/2003 | Samuelsson et al. |
| 7,465,297 B2 | 12/2008 | Watanabe et al. |
| 7,549,981 B2 | 6/2009 | Tanio et al. |
| 7,597,690 B2 | 10/2009 | Tanio et al. |
| 7,621,899 B2 | 11/2009 | Fujikawa et al. |
| 7,648,490 B2 | 1/2010 | Kuroda et al. |
| 2002/0143309 A1 | 10/2002 | Glasgow et al. |
| 2002/0193766 A1* | 12/2002 | Gell et al. ............... 604/385.03 |
| 2006/0282059 A1 | 12/2006 | Fujikawa et al. |
| 2010/0145296 A1* | 6/2010 | Kudo et al. ............. 604/385.01 |

* cited by examiner

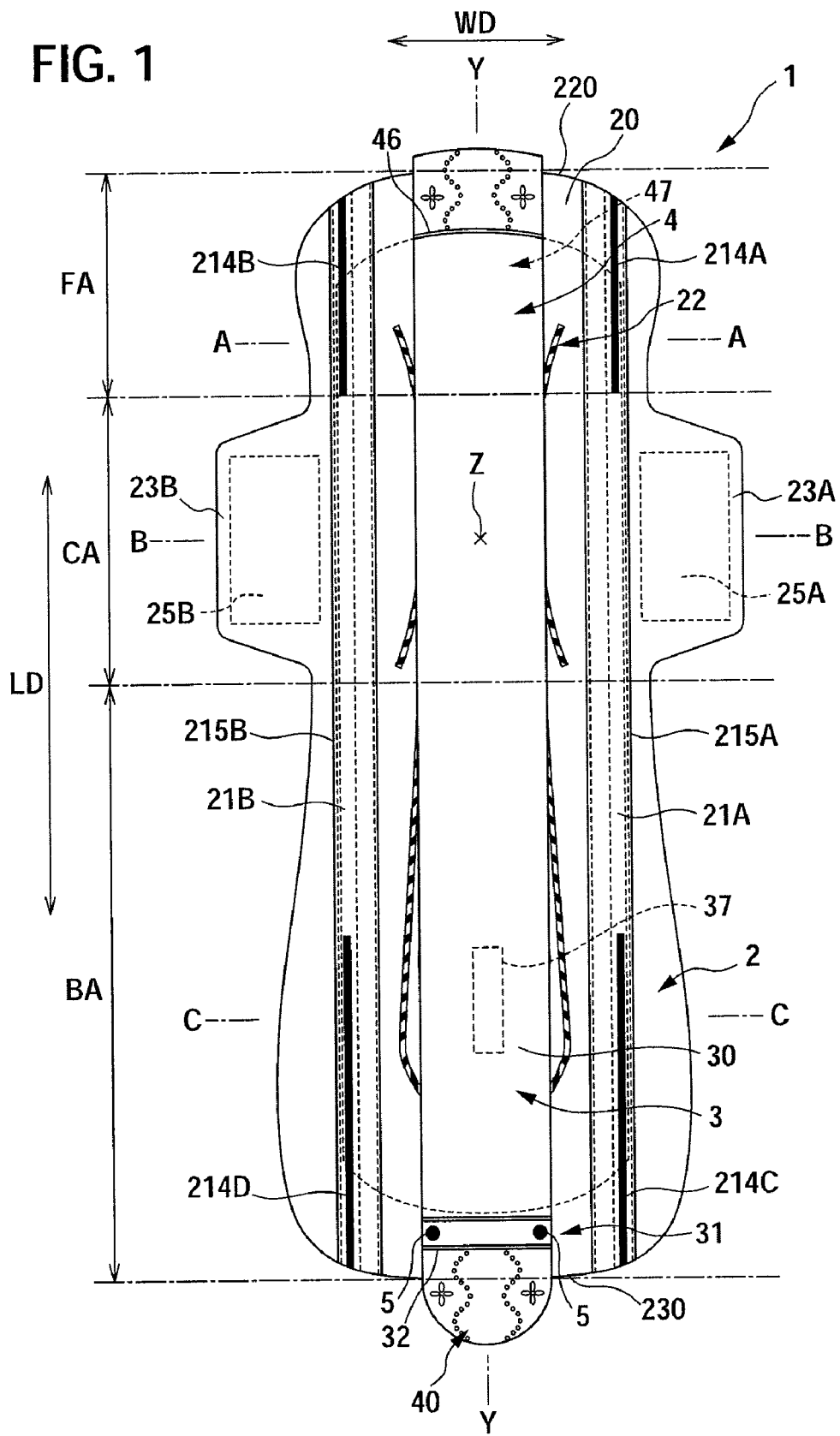

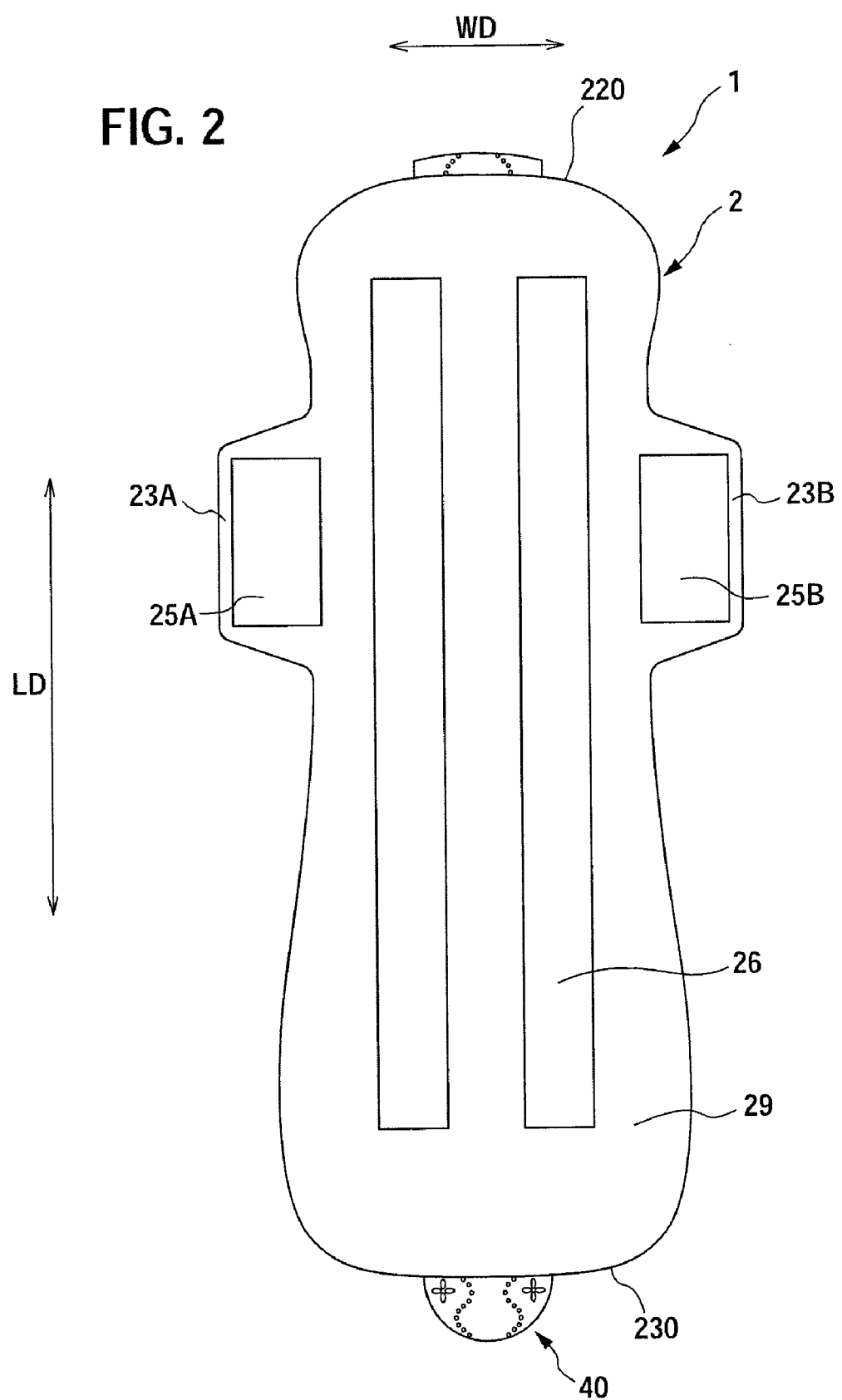

ABSORPTIVE ARTICLE

RELATED APPLICATIONS

The present application is based on International Application Number PCT/JP2007/063504 filed Jul. 5, 2007, and claims priority from Japanese Application Number 2006-186141, filed Jul. 5, 2006, the disclosures of which are hereby incorporated by reference herein in their entirety.

TECHNICAL FIELD

The present invention relates to an absorbent article.

BACKGROUND ART

Conventionally, as an absorbent article for absorbing a predetermined liquid such as menstrual blood, an absorbent article that is entirely formed in a sheet-like shape, including an absorbent layer for absorbing the predetermined liquid, a liquid permeable top sheet for covering a skin contacting surface of the absorbent layer, and a liquid impermeable back surface sheet for covering a clothing side surface of the absorbent layer, can be exemplified. Such an absorbent article, which is substantially sheet-shaped, is used in contact with an excretory part of the predetermined liquid such as menstrual blood, directly absorbs the predetermined liquid such as menstrual blood discharged from the excretory part. Various improvements have been made thereto in order to prevent menstrual blood and the like, which runs along a predetermined groove of a wearer's body, from contacting clothing and the like.

An example of a means for preventing menstrual blood from leaking is a means for absorbing menstrual blood by providing wings so as to project in the width direction at both side portions of an absorbent article, folding back the wings toward underwear to fix the absorbent article, and raising an absorbent body in the vicinity of an excretion area of the menstrual blood toward the excretory opening to make an absorbent body tightly fit the excretion area. However, even such an absorbent article cannot, in some cases, suitably follow changes in the movement of the wearer's body and the shape caused by the movement.

On the other hand, an absorbent article including a lower absorbent body fixed to a main body portion of the absorbent article and an upper absorbent body provided separately from the lower absorbent body and so adapted that an intermediate sheet having elastic stretchability arranged in the longitudinal direction so as to be sandwiched between the upper absorbent body and the lower absorbent body pushes up the upper absorbent body to tightly fit the wearer's body, in order to enhance the property of following the excretion area has been proposed (see, for example, Patent Document 1).

[Patent Document] Japanese Unexamined Patent Application Publication No. 2000-152957

DISCLOSURE OF THE INVENTION

Problems to be Solved by the Invention

However, an absorbent article in Patent Document 1 has an uppermost surface thereof which becomes wide in the width direction and forming a plane when worn because an upper absorbent body is wholly fixed along the longitudinal direction to a lower absorbent body of a sanitary napkin and is fixed in the width direction at both ends of the lower absorbent body. Therefore, a predetermined space is produced between the upper absorbent body and a groove of the wearer's body. Therefore, the upper absorbent body cannot come into contact with and tightly fit the excretion area in an inner part of the groove of the wearer's body without any clearance, so that menstrual blood may leak.

Furthermore, the upper absorbent body can follow slight lateral movement of the wearer's body by being deformed. However, the upper absorbent body cannot follow such movement of the wearer's body or underwear that it is greatly dislocated in the width direction and longitudinal movement of the wearer's body or underwear.

In addition, since the upper absorbent body is completely fixed to the lower absorbent body along the longitudinal direction, when a user wears the sanitary napkin with the sanitary napkin attached to the underwear, the sanitary napkin is worn at a position where it cannot be seen by the user. Thus, the user cannot always wear the sanitary napkin such that the upper absorbent body sufficiently fits tightly with the groove of the wearer's body. In a case where the user cannot wear the sanitary napkin so as to tightly fit the groove of the wearer's body, a predetermined space is produced between the upper absorbent body and the excretory opening so that the menstrual blood may leak.

The present invention has been made in view of the foregoing problems and has an objective of providing an absorbent article that includes an absorbent body capable of following the wearer's body.

Means for Solving the Problems

In a first aspect, an absorbent article includes a substantially rectangular first absorbent body (e.g., a base absorbent body 2 in a first embodiment, described later), a second absorbent body (e.g., a top absorbent body 3 in the first embodiment, described later) arranged along a longitudinal direction of the first absorbent body on a skin contacting side of the first absorbent body, a fixing portion that fixes the first absorbent body and the second absorbent body such that at least one edge of the second absorbent body in the longitudinal direction is a free end, and a locking portion that is arranged on a skin noncontacting side opposite to the skin contacting side of the second absorbent body and can lock the first absorbent body and the second absorbent body.

According to a second aspect, in the absorbent article as described in the first aspect, the absorbent article has a front edge serving as an outer edge in the longitudinal direction and close to a first position that contacts with an excretion area in a state of wearing on a wearing target, and a rear edge far from the first position, in which the fixing portion is formed between the first position and the front edge.

According to a third aspect, in the absorbent article as described in the first or second aspect, the locking portion is arranged on a side of the free end.

According to a fourth aspect, in the absorbent article as described in any one of the first to third aspects, the first absorbent body includes a central portion where the second absorbent body can be arranged on a surface thereof on which the second absorbent body is arranged, the central portion includes a first absorbent body side surface sheet arranged so as to cover a top surface of the central portion, and the first absorbent body side surface sheet is formed of a non-woven fabric that can be engaged with the locking portion.

According to a fifth aspect, in the absorbent article as described in any one of the first to fourth aspects, an elastic member is arranged on the skin contacting side of the first absorbent body side surface sheet at a rear edge side of the first absorbent body.

In a sixth aspect, the absorbent article as described in any one of the first to fifth aspects further includes a handle portion at the free end in the second absorbent body.

According to a seventh aspect, in the absorbent article as described in the sixth aspect, flexural rigidity (B) of the handle portion is 0.1 to 1.2 ($10^{-4}$ N·m²/m).

According to an eighth aspect, in the absorbent article as described in the sixth or seventh aspect, flexure recovery (2 HB) of the handle portion is no greater than 10 ($10^{-2}$ N·m²/m).

According to a ninth aspect, in the absorbent article as described in any one of the sixth to eighth aspects, the handle portion is arranged substantially at a center in a width direction of the first absorbent body in a state where the handle portion arranged along a central portion, where the second absorbent body is arranged, in the first absorbent body.

According to a tenth aspect, in the absorbent article as described in any one of sixth to ninth aspects, a top surface of the handle portion is formed in a concave and convex shape.

In an eleventh aspect, an absorbent article includes a substantially rectangular first absorbent body, a second absorbent body arranged along a longitudinal direction of the first absorbent body on the skin contacting side in the first absorbent body, a fixing portion that fixes the first absorbent body with the second absorbent body such that at least one end portion in the longitudinal direction of the second absorbent body is a free end, and a locking portion that is arranged on a skin noncontacting side which is a surface of an opposite side to the skin contacting side of the second absorbent body, is covered by the first absorbent body in a state in which the second absorbent body is not spaced apart from the first absorbent body, and is exposed in a state in which the second absorbent body is spaced apart from the first absorbent body.

Effects of the Invention

According to the present invention, an absorbent article can be provided that includes an absorbent body capable of following the wearer's body.

BRIEF DESCRIPTION OF THE DRAWINGS

FIG. 1 is a plan view of an absorbent article according to a first embodiment of the present invention;

FIG. 2 is a back view of the absorbent article according to the first embodiment of the present invention;

PREFERRED MODE FOR CARRYING OUT THE INVENTION

Figure 3A:
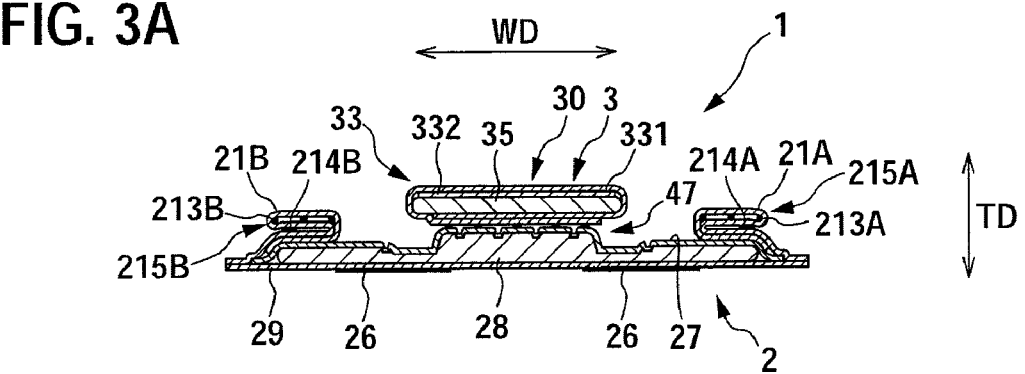
FIG. 3A is a cross-sectional view of FIG. 1 showing the absorbent article according to the first embodiment of the present invention.
Figure 3B:
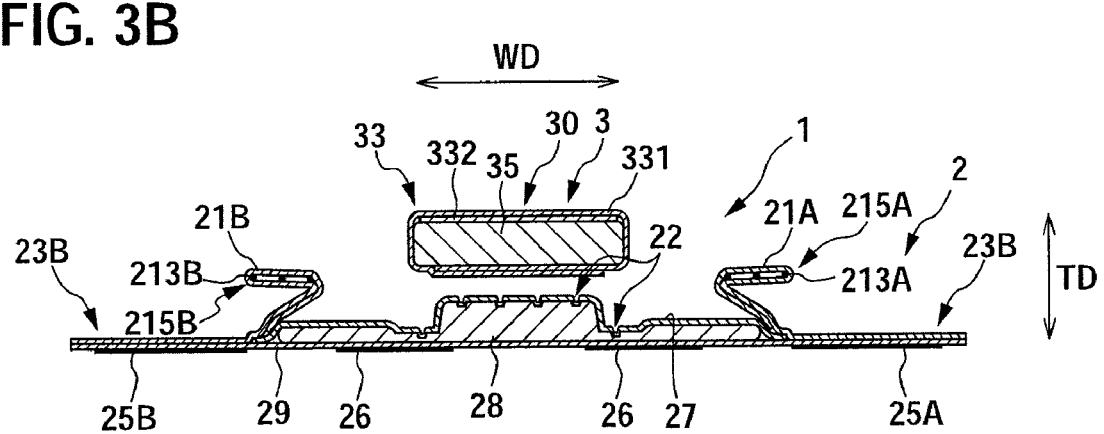
FIG. 3B is a cross-sectional view of FIG. 1 showing the absorbent article according to the first embodiment of the present invention.
Figure 3C:
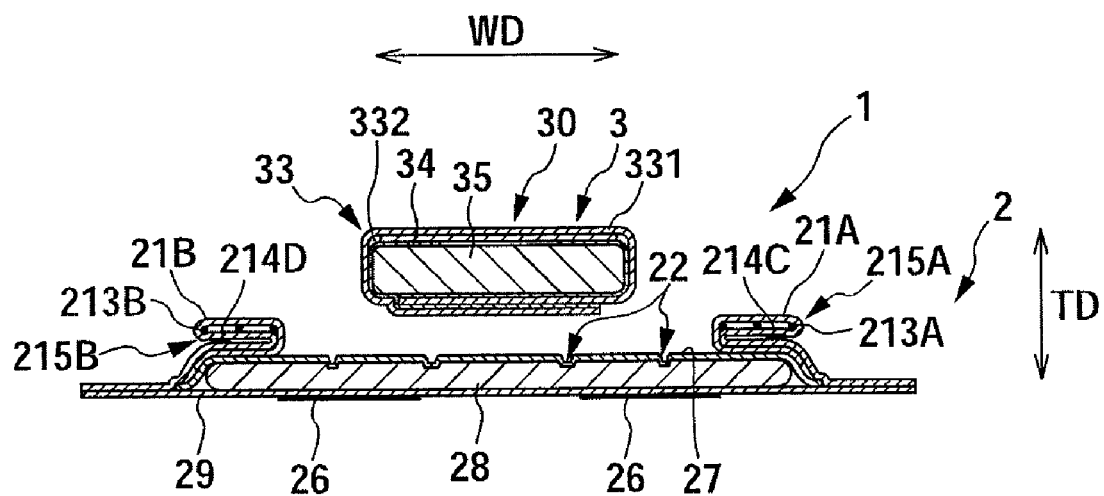
FIG. 3C is a transverse sectional view of FIG. 1 showing the absorbent article according to the first embodiment of the present invention.
Figure 4:
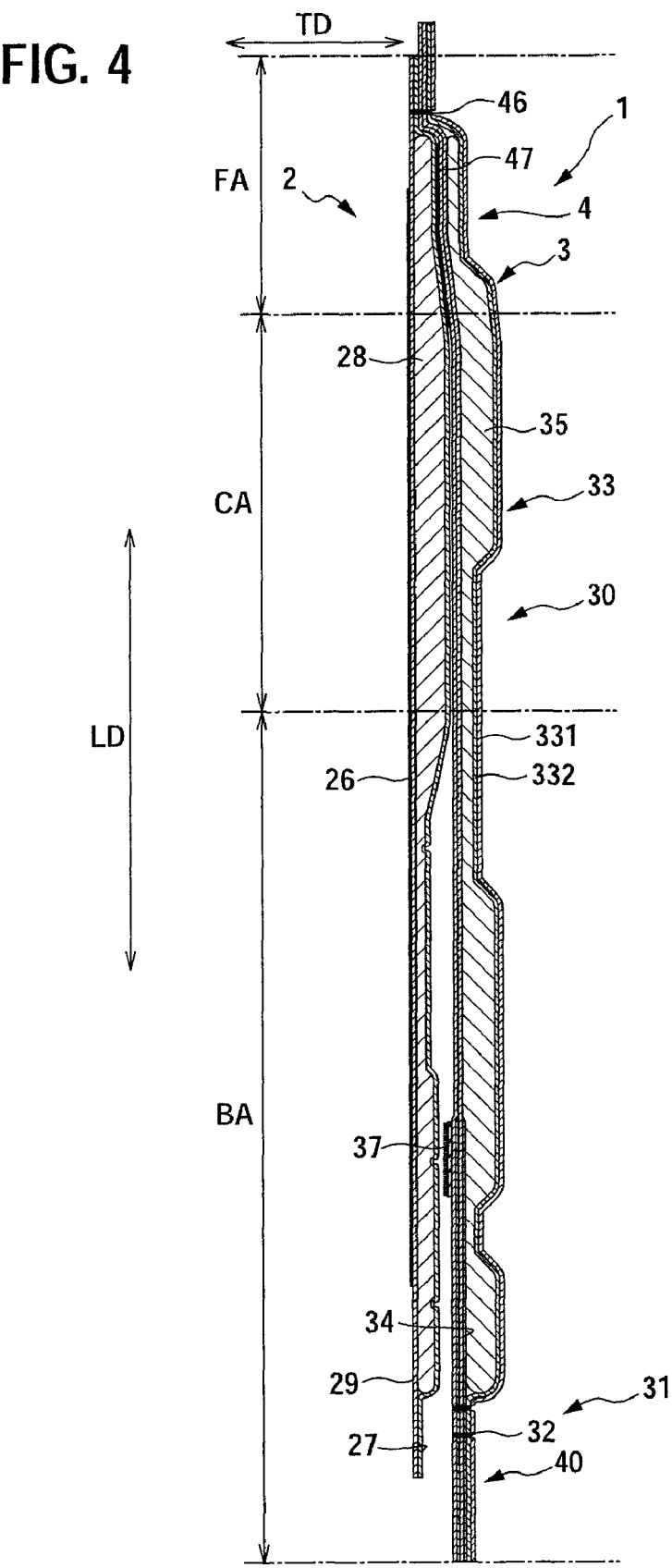
FIG. 4 is a longitudinal sectional view taken along a line Y-Y in FIG. 1 of the absorbent article according to the first embodiment of the present invention.
Figure 5:
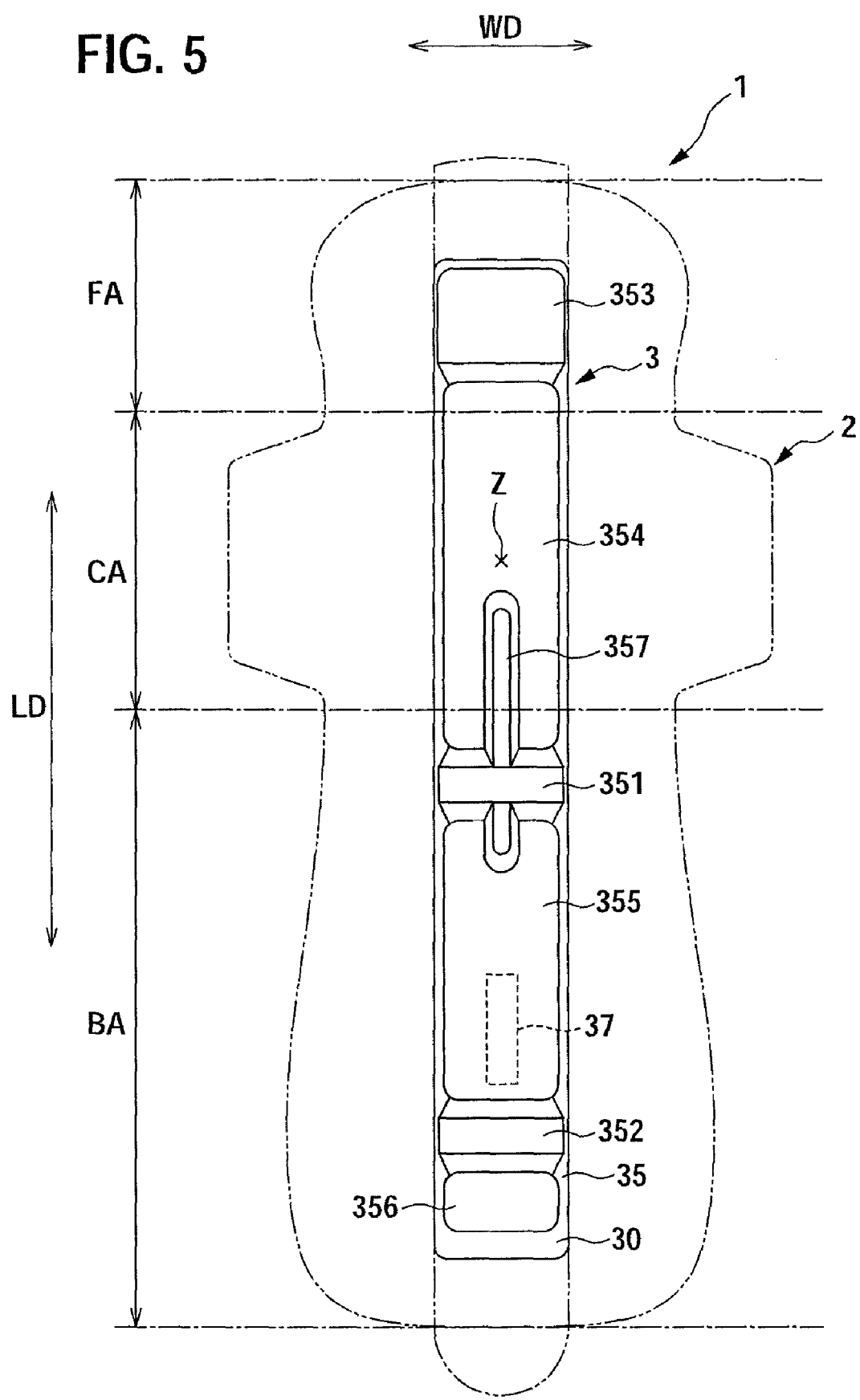
FIG. 5 is a diagram showing an absorbent core arranged on a top absorbent body according to the first embodiment of the present invention.
Figure 6:
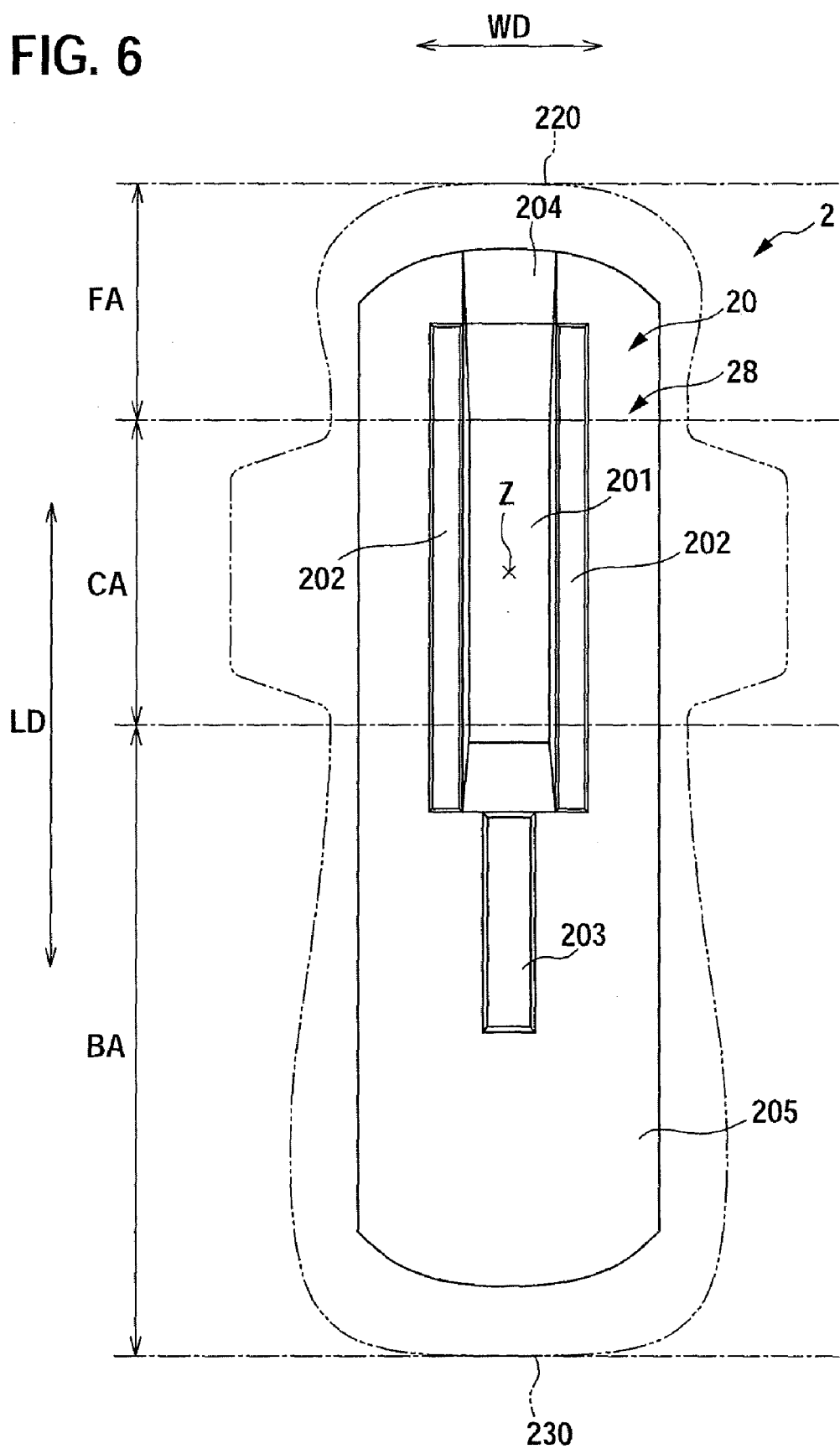
FIG. 6 is a diagram showing an absorbent core arranged in a base absorbent body according to the first embodiment of the present invention.
Figure 7:
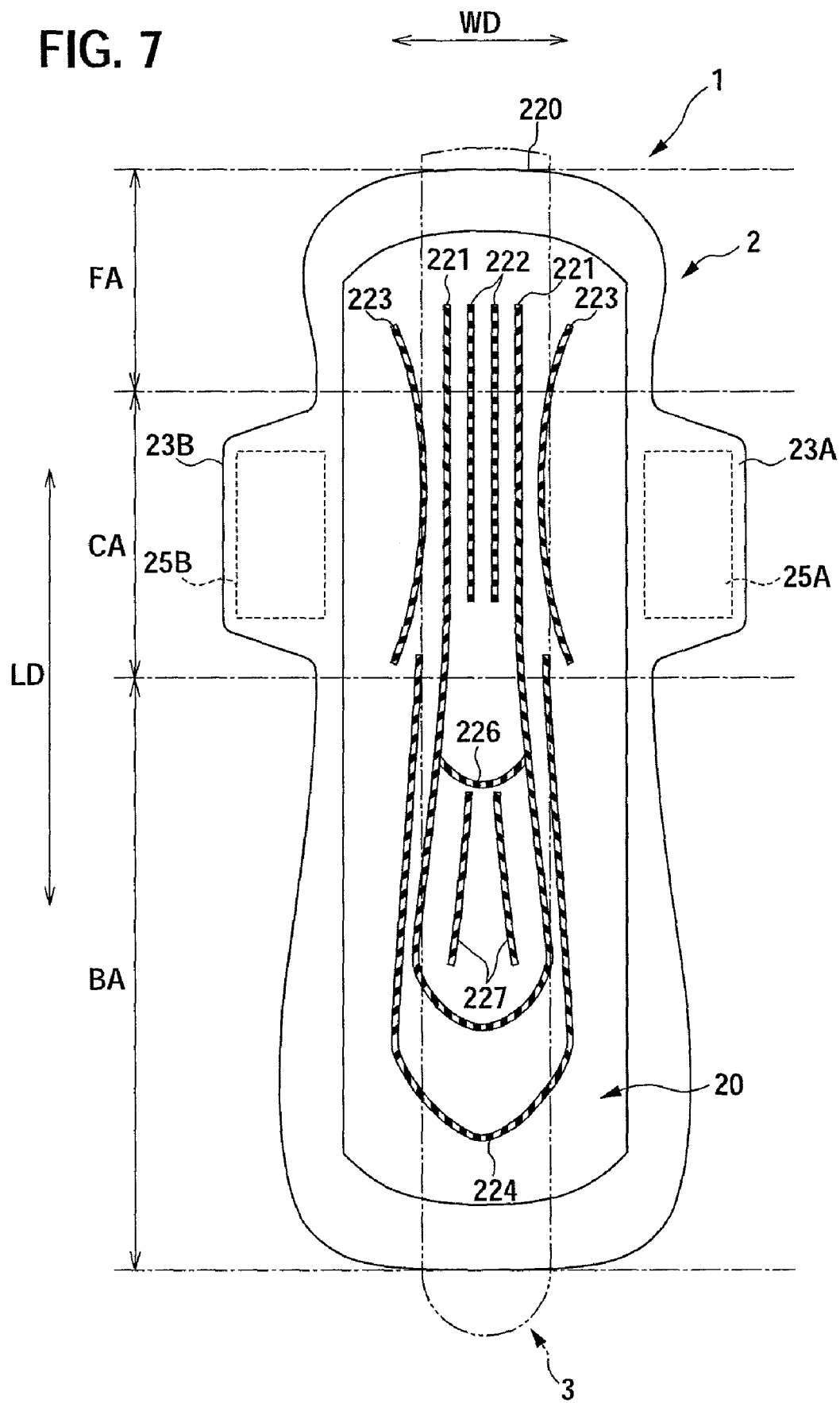
FIG. 7 is a diagram showing compressed grooves in a base absorbent body according to the first embodiment of the present invention.
Figure 8:
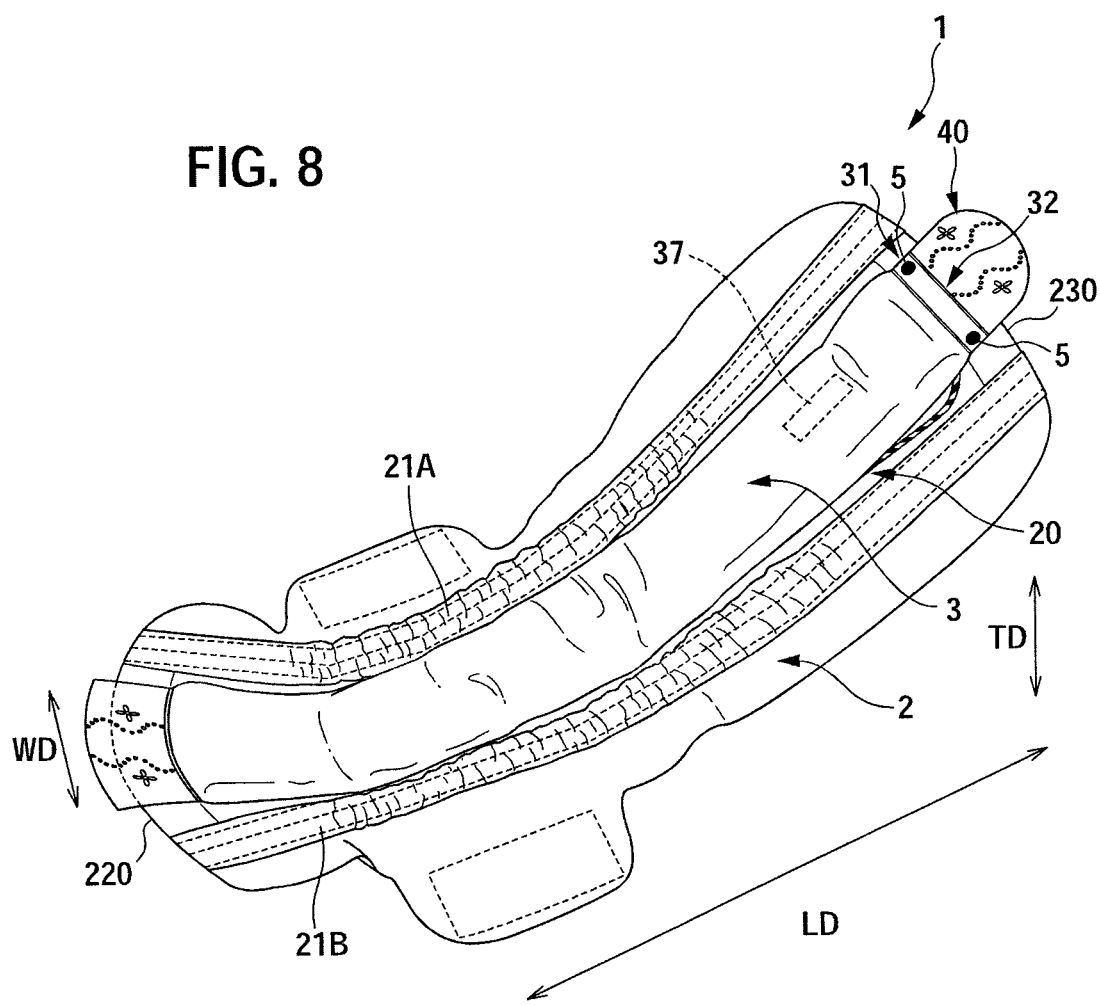
FIG. 8 is a perspective view in a worn state of the absorbent article according to the first embodiment of the present invention.
Figure 9:
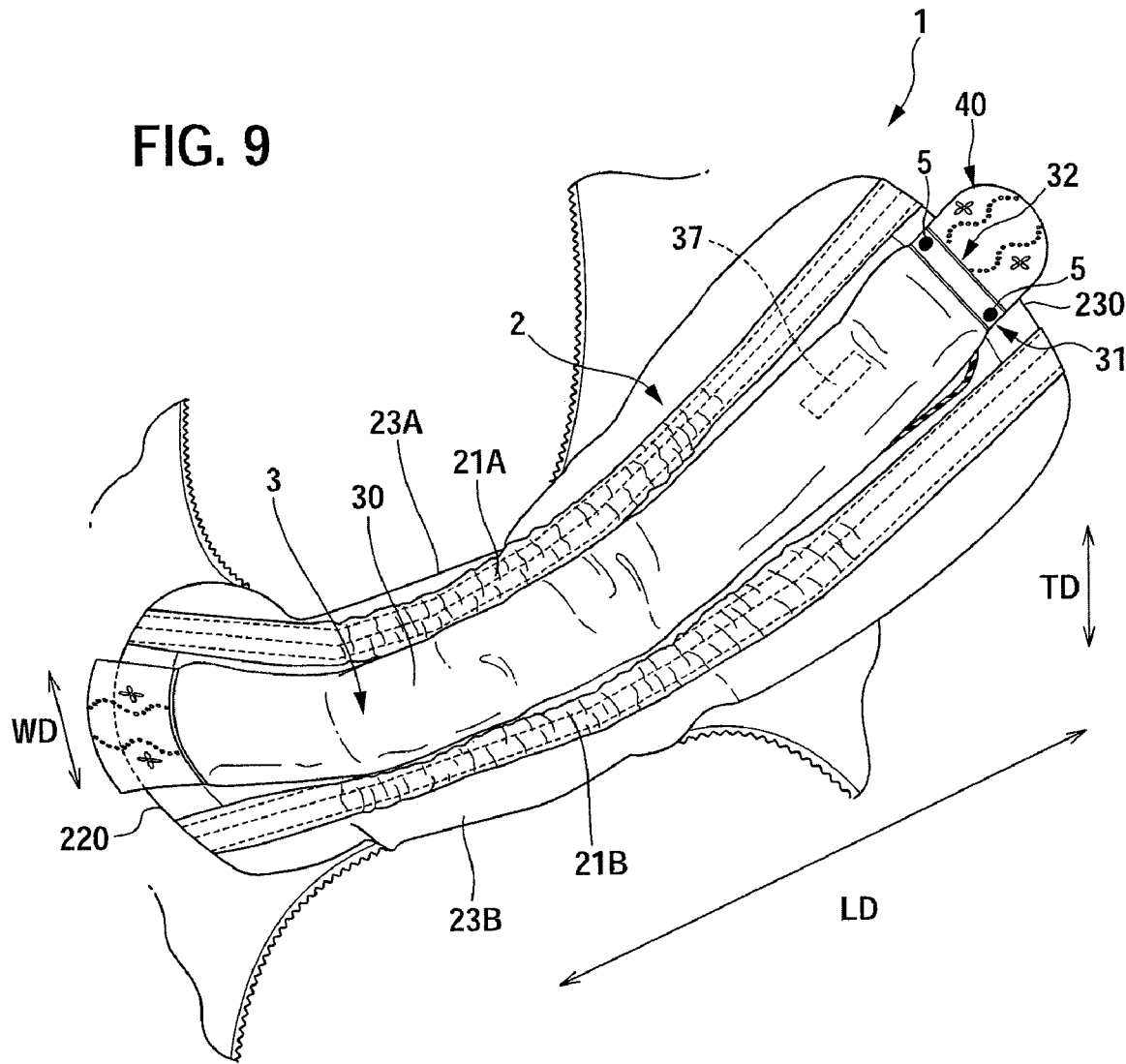
FIG. 9 is a perspective view in a worn state of the absorbent article according to the first embodiment of the present invention.
Figure 10:
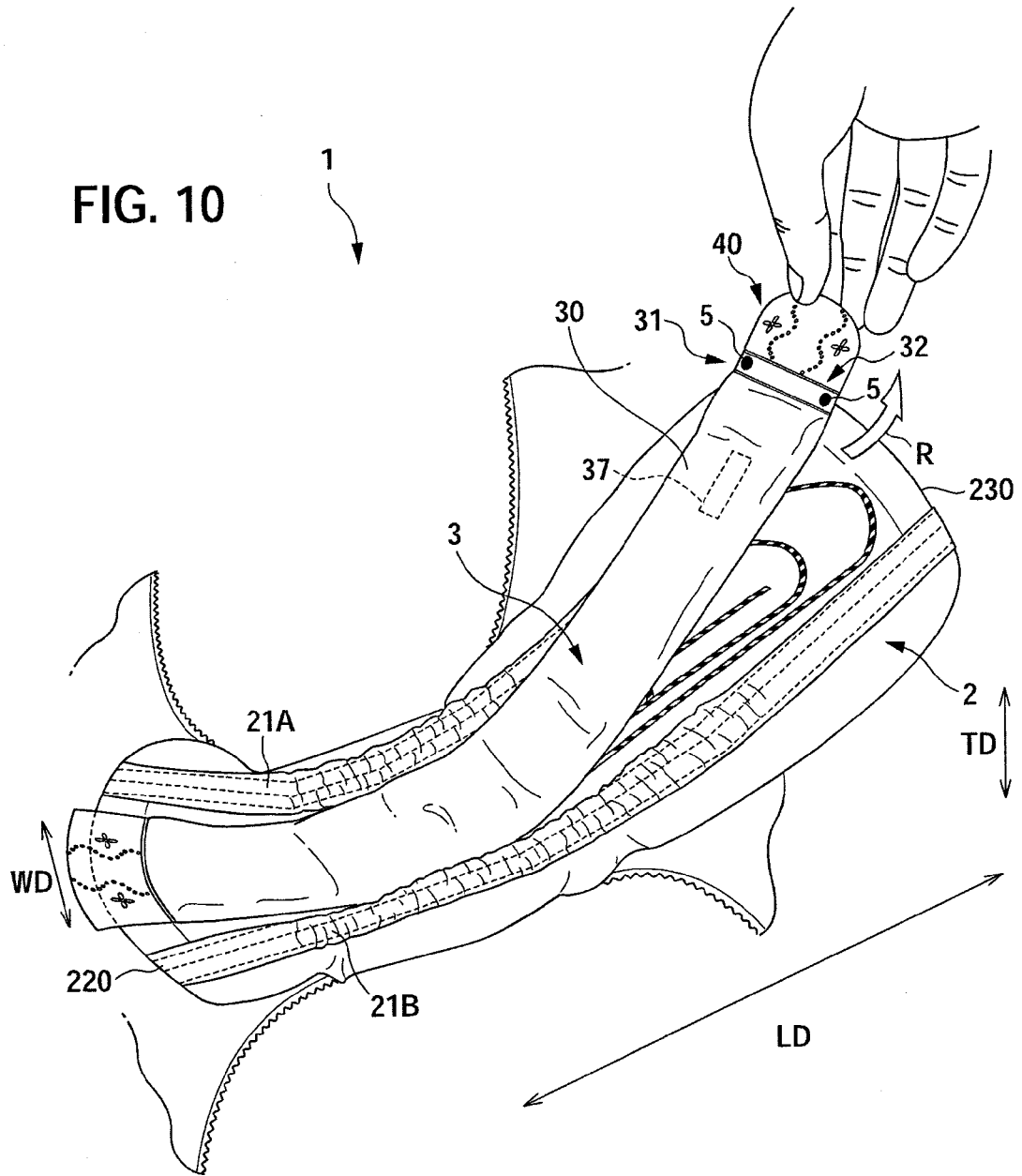
FIG. 10 is a perspective view in a worn state of the absorbent article according to the first embodiment of the present invention.
Figure 11:
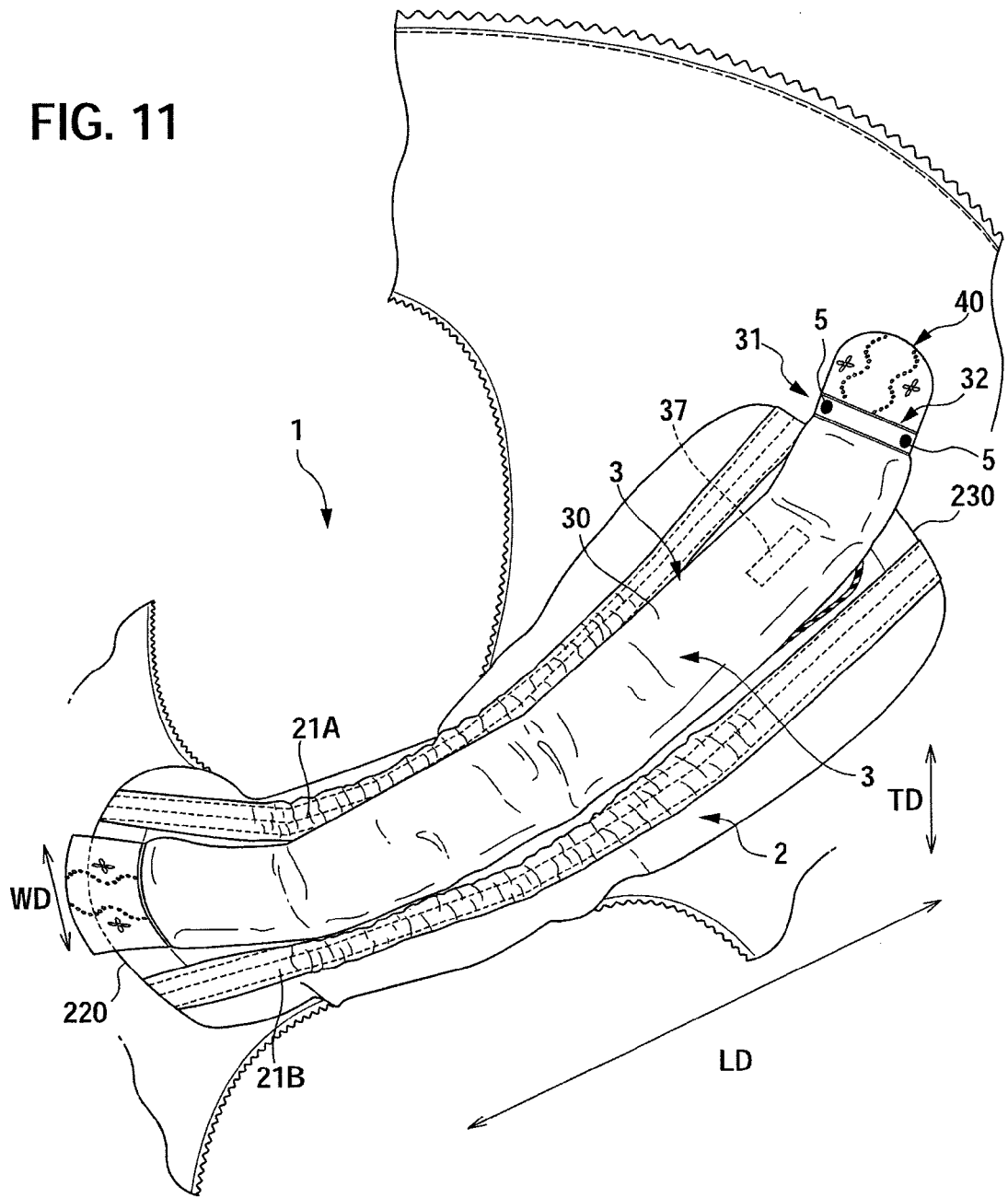
FIG. 11 is a perspective view in a worn state of the absorbent article according to the first embodiment of the present invention.

FIG. 1 is a plan view of an absorbent article according to a first embodiment of the present invention. FIG. 2 is a back view of the absorbent article according to the first embodiment of the present invention. FIG. 3A is a cross-sectional view taken along a line A-A in FIG. 1 of the absorbent article according to the first embodiment of the present invention. FIG. 3B is a transverse sectional view taken along a line B-B in FIG. 1 of the absorbent article according to the first embodiment of the present invention. FIG. 3C is a transverse sectional view taken along a line C-C in FIG. 1 of the absorbent article according to the first embodiment of the present invention. FIG. 4 is a longitudinal sectional view taken along a line Y-Y in FIG. 1 of the absorbent article according to the first embodiment of the present invention. FIG. 5 is a diagram showing an absorbent core arranged on a top absorbent body according to the first embodiment of the present invention. FIG. 6 is a diagram showing an absorbent core arranged in a base absorbent body according to the first embodiment of the present invention. FIG. 7 is a diagram showing compressed grooves in a base absorbent body according to the first embodiment of the present invention. FIG. 8 is a perspective view in a worn state of the absorbent article according to the first embodiment of the present invention. FIG. 9 is a perspective view in a worn state of the absorbent article according to the first embodiment of the present invention. FIG. 10 is a perspective view in a worn state of the absorbent article according to the first embodiment of the present invention. FIG. 11 is a perspective view in a worn state of the absorbent article according to the first embodiment of the present invention.

Figure 12A:
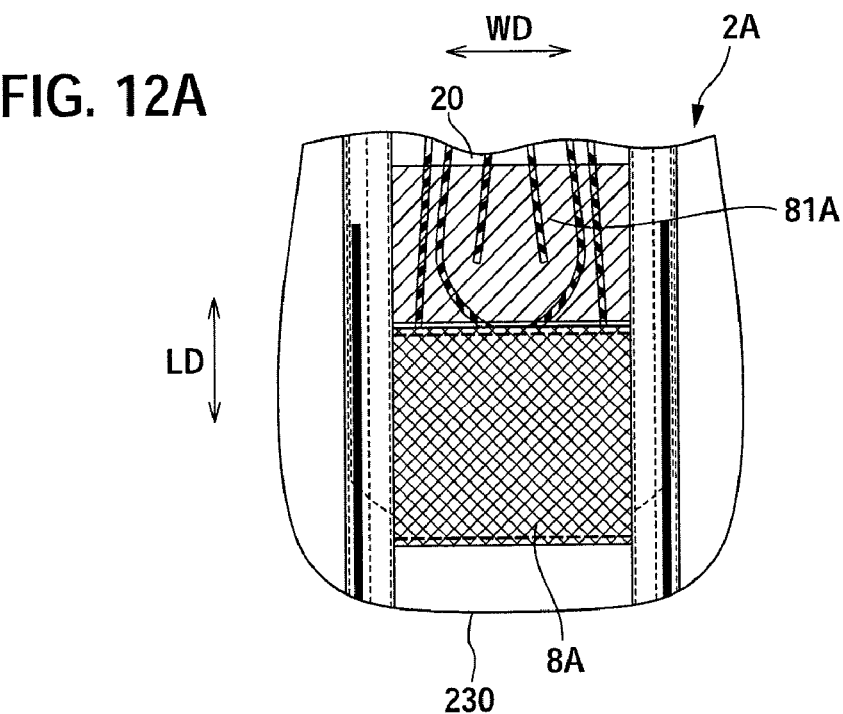
FIG. 12A is a plan view of a top absorbent body according to a second embodiment of the present invention.
Figure 12B:
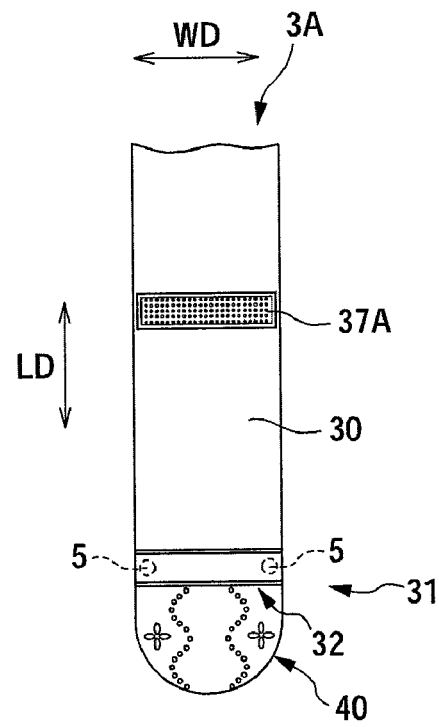
FIG. 12B is a plan view of the top absorbent body according to the second embodiment of the present invention.
Figure 13A:
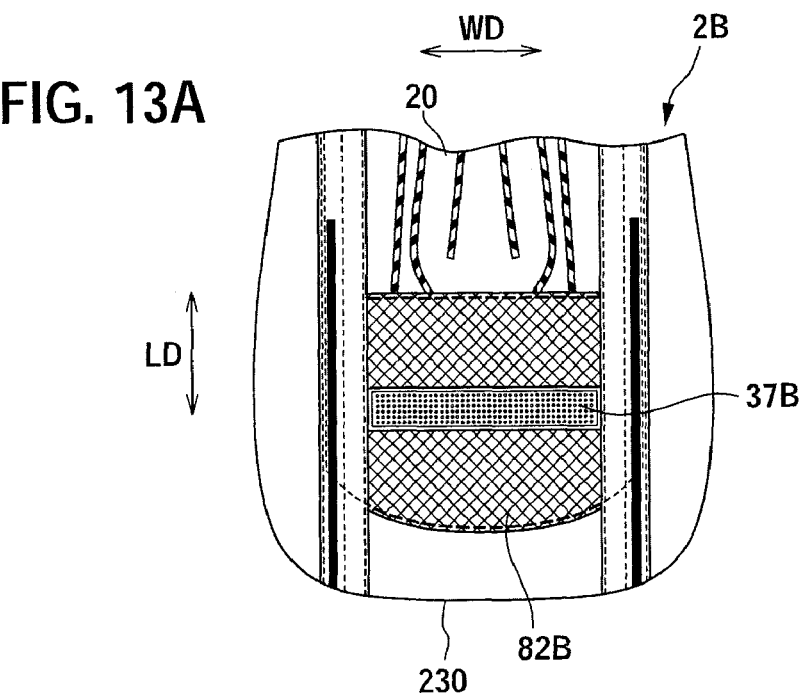
FIG. 13A is a plan view of an absorbent article according to a third embodiment of the present invention.
Figure 13B:
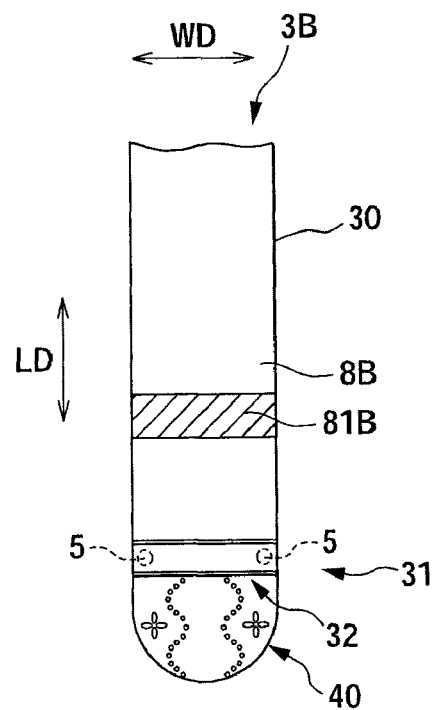
FIG. 13B is a plan view of the absorbent article according to the third embodiment of the present invention.
Figure 14A:
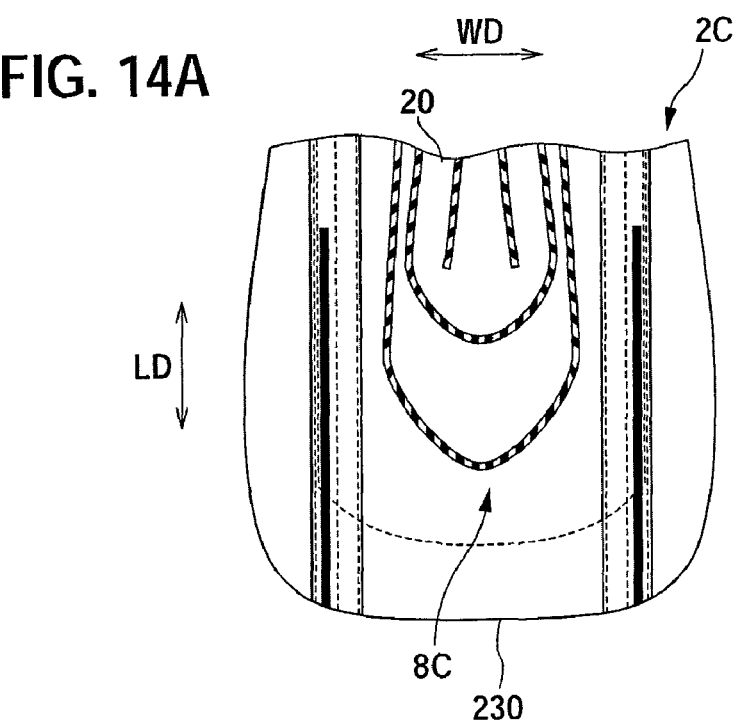
FIG. 14A is a plan view of an absorbent article according to a fourth embodiment of the present invention.
Figure 14B:
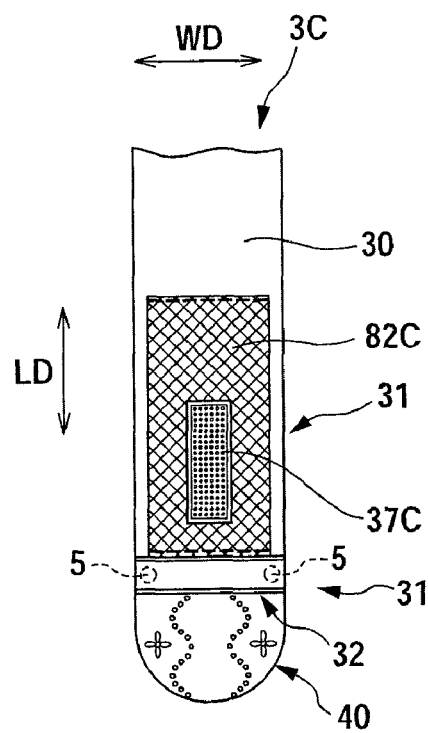
FIG. 14B is a plan view of the absorbent article according to the fourth embodiment of the present invention.
Figure 15A:
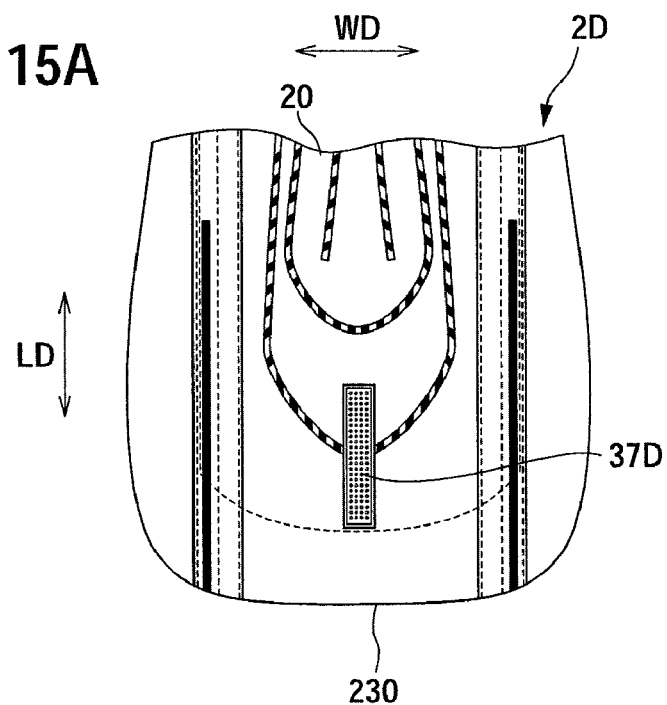
FIG. 15A is a plan view of an absorbent article according to a fifth embodiment of the present invention.
Figure 15B:
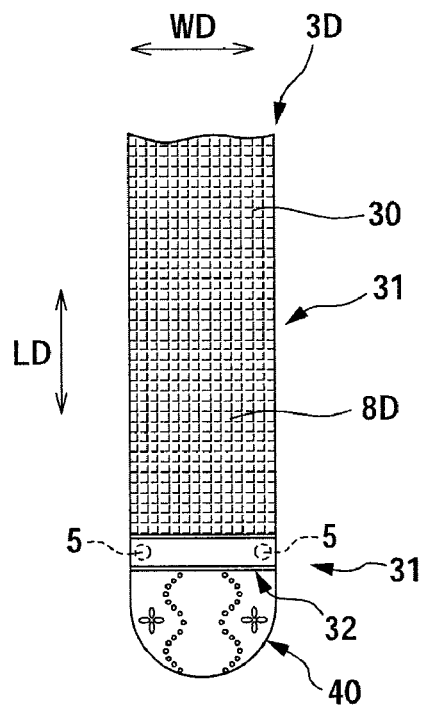
FIG. 15B is a plan view of the absorbent article according to the fifth embodiment of the present invention.
Figure 16:
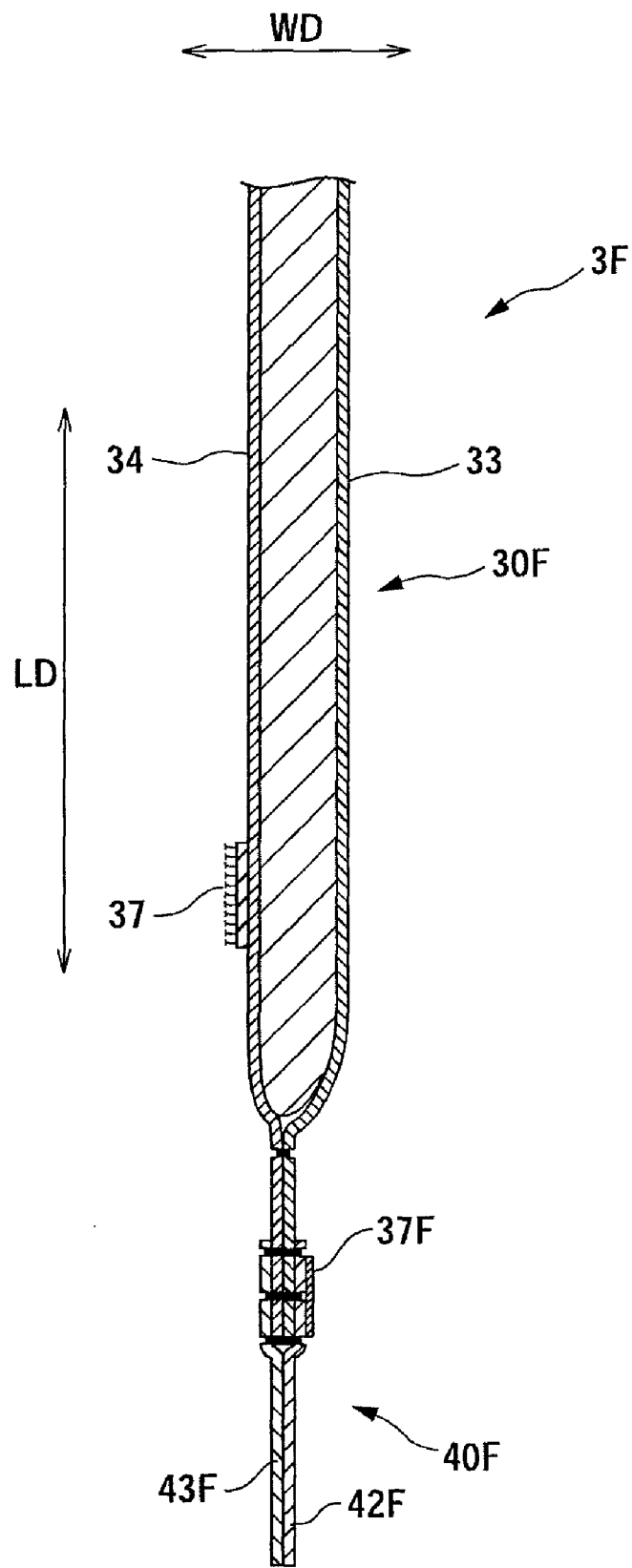
FIG. 16 is a cross-sectional view of a top absorbent body according to a sixth embodiment of the present invention.
Figure 17:
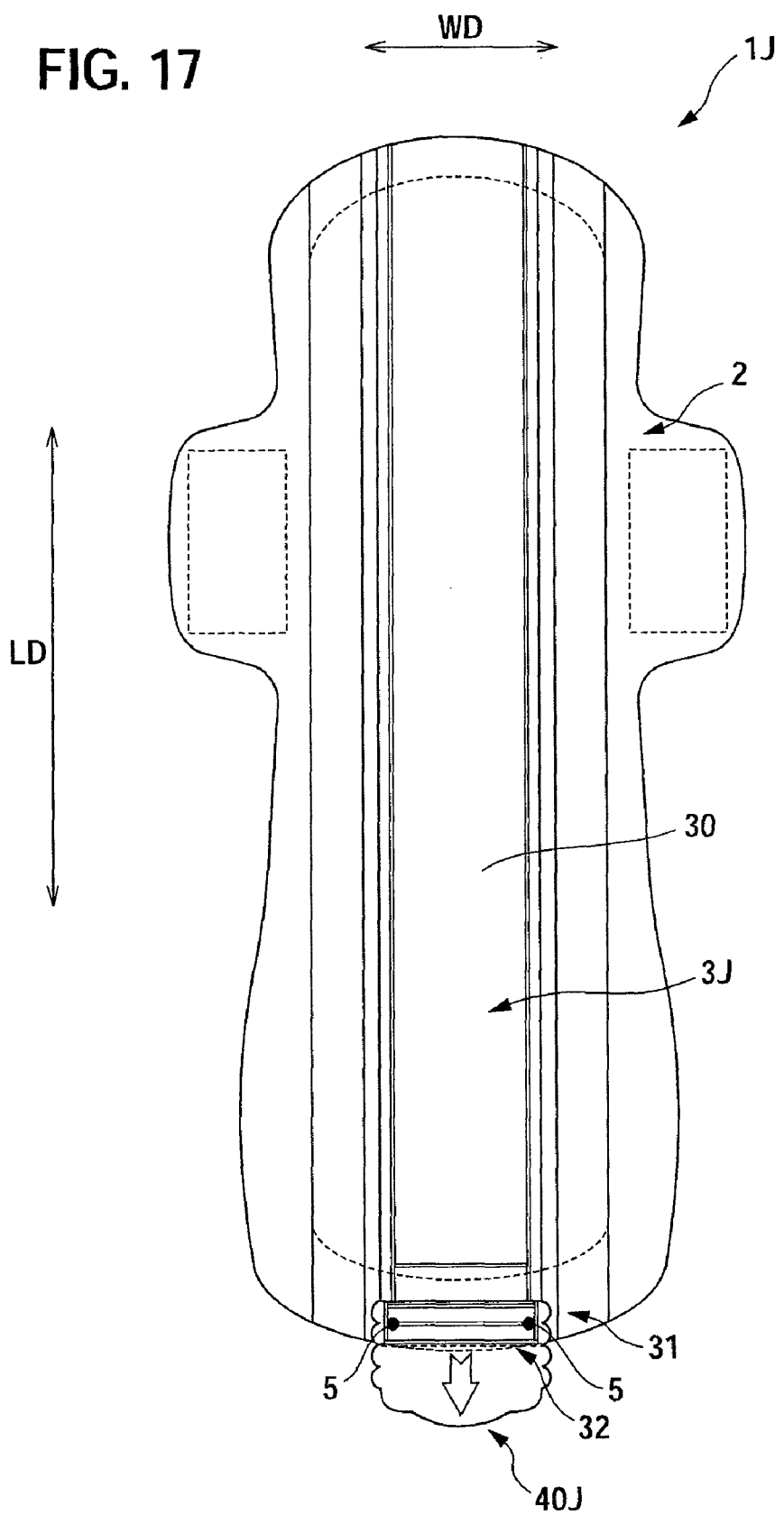
FIG. 17 is a plan view of an absorbent article according to a seventh embodiment of the present invention.
Figure 18:
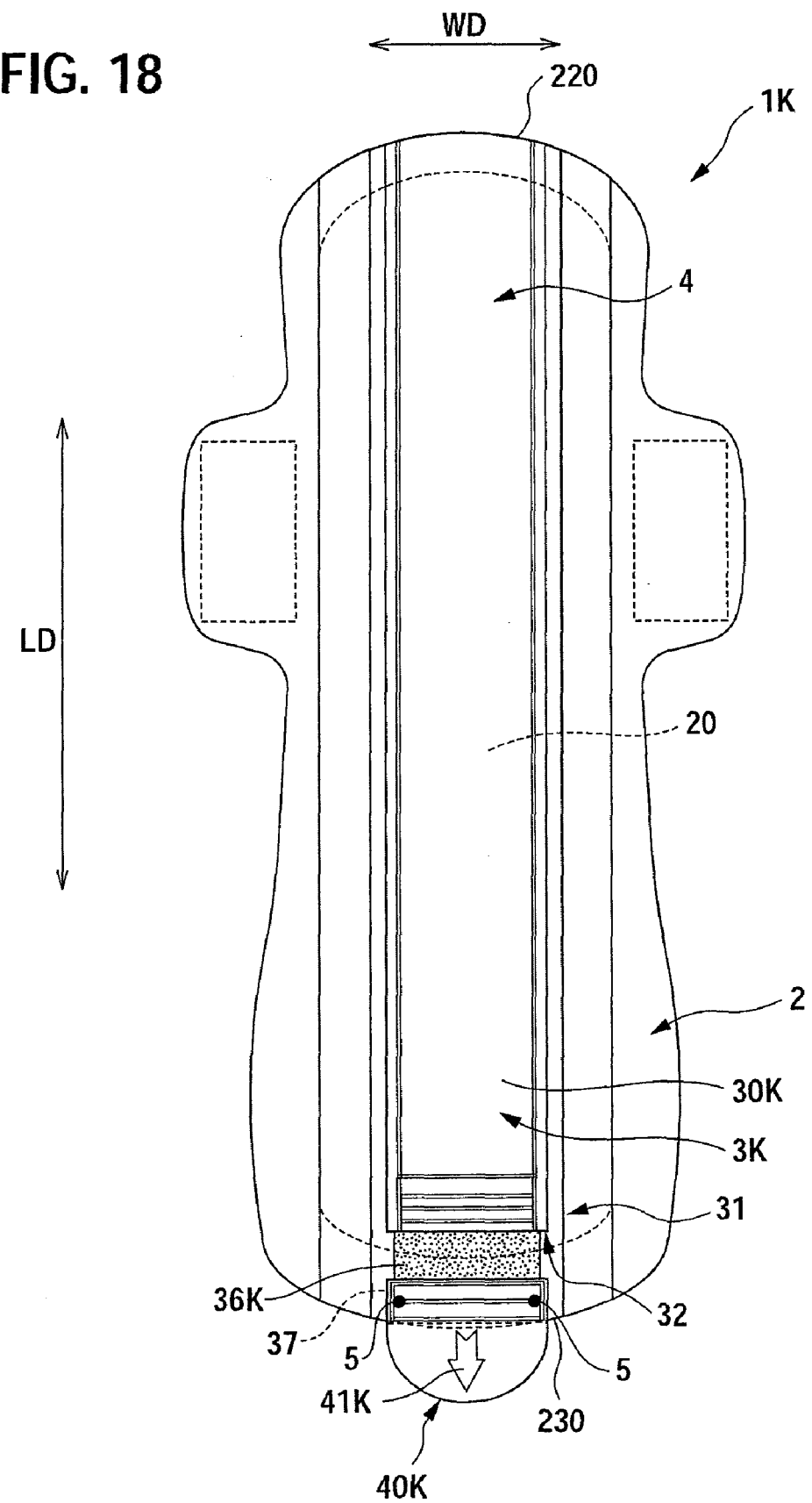
FIG. 18 is a plan view of an absorbent article according to an eighth embodiment of the present invention.
Figure 19:
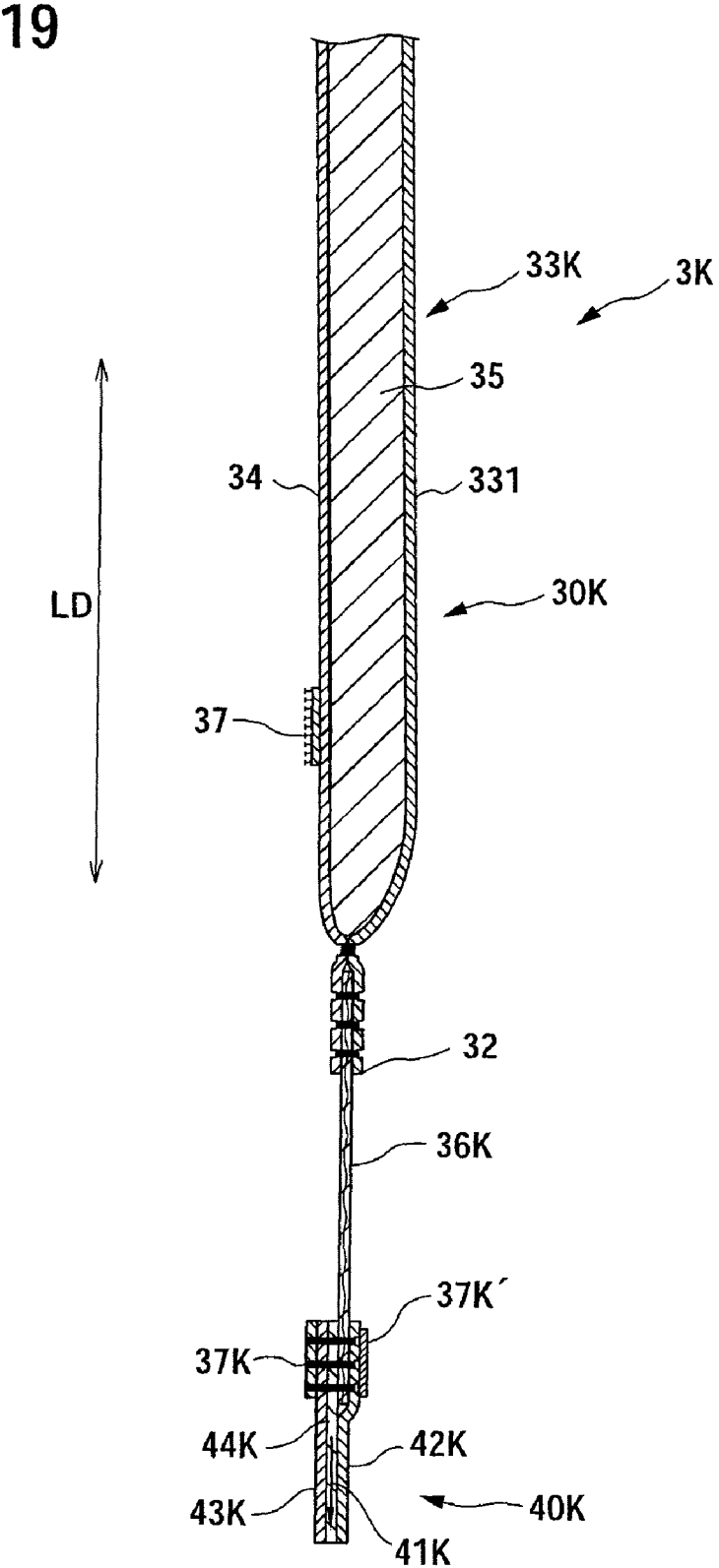
FIG. 19 is an enlarged longitudinal sectional view of a top absorbent body according to the absorbent article in the eighth embodiment of the present invention.

FIG. 12A is an enlarged plan view on the side of a rear edge of a base absorbent body according to a second embodiment. FIG. 12B is an enlarged back view on the side of a free end of a top absorbent body according to the second embodiment. FIG. 13A is an enlarged plan view on the side of a rear edge of a base absorbent body according to a third embodiment. FIG. 13B is an enlarged back view on the side of a free end of a top absorbent body according to the third embodiment. FIG. 14A is an enlarged plan view on the side of a rear edge of a base absorbent body according to a fourth embodiment. FIG. 14B is an enlarged back view on the side of a free end of a top absorbent body according to the fourth embodiment. FIG. 15A is an enlarged plan view on the side of a rear edge of a base absorbent body according to a fifth embodiment. FIG. 15B is an enlarged back view on the side of a free end of a top absorbent body in the fifth embodiment. FIG. 16 is a cross-sectional view of a top absorbent body according to a sixth embodiment. FIG. 17 is a plan view of an absorbent article according to a seventh embodiment of the present invention. FIG. 18 is a plan view of an absorbent article according to an eighth embodiment of the present invention. FIG. 19 is an enlarged longitudinal sectional view of a top absorbent body in the absorbent article according to the eighth embodiment of the present invention.

1. Overview of Absorbent Article

A summary concerning an absorbent article according to the present invention will be described according to an absorbent article 1 in a first embodiment of the present invention shown in FIGS. 1 to 11.

1. First Embodiment

An absorbent article 1 according to a first embodiment of the present invention will be described with reference to FIGS. 1 to 11.

1.1. Overview

As shown in FIGS. 1 to 11, the absorbent article 1 according to the present embodiment is an absorbent article of substantially rectangular shape. The absorbent article 1 includes a substantially rectangular base absorbent body 2, and a top absorbent body 3 arranged along a longitudinal direction LD of the base absorbent body 2 on one surface of the base absorbent body 2. Regarding the top absorbent body 3, at least one portion thereof in the longitudinal direction LD is fixed to the base absorbent body 2, and the end thereof that is not fixed thereto is a free end 31 spaced apart from the base absorbent body 2 with the fixed part taken as a starting point and independently operable.

The base absorbent body 2 is arranged on the garment side and absorbs a predetermined liquid such as menstrual blood that cannot be absorbed by the top absorbent body 3. In the base absorbent body 2, a strip-shaped central portion 20 is formed along the longitudinal direction LD nearly at the center in a width direction WD of the base absorbent body 2. Wings 23A and 23B are respectively formed so as to project outward in the width direction WD on both sides in the width direction WD of the absorbent article 1.

Here, the absorbent article 1 has a position Z as a first position with which the body excretory opening area is supposed to come into contact. The position Z is an intersection of a centerline Y extending along the longitudinal direction LD at the center in the width direction WD of the absorbent article 1 and a centerline B-B extending along the width direction WD at the center in the longitudinal direction LD of the wings 23A and 23B. In other words, the wings 23A and 23B are formed so as to satisfy the abovementioned positional relationship. In addition, in the base absorbent article 2, a region where the wings 23A and 23B are arranged, a region ahead of the region where the wings 23A and 23B are arranged, and a region behind the position where the wings 23A and 23B are arranged are taken as a central region CA, an anterior region FA, and a posterior region BA, respectively. Details thereof are as described later.

The top absorbent body 3 is layered and arranged on the central portion 20 in the base absorbent body 2. The top absorbent body 3 comes into direct contact with the excretory opening or the like of the wearer's body during use, to absorb a predetermined liquid such as menstrual blood. The top absorbent body 3 is fixed to the base absorbent body 2 by a fixing portion 4 provided at one portion in the longitudinal direction LD. Then, an end portion of a side not fixed by the fixing portion 4 top absorbent body becomes a free end 31. When the top absorbent body 3 is fixed to the base absorbent body 2 at a position other than the end portion thereof, a side far from the fixing portion 4 in the longitudinal direction LD, for example, is a free end 31.

A handle portion 40 is arranged on the side of the free end 31 in the top absorbent body 3. Then, When the absorbent article 1 is employed, the handle portion 40 is gripped, to separate a region, on the side of the free end 31, of the top absorbent body 3 from the base absorbent body 2 with the fixing portion 4 as a starting point, thereby allowing the top absorbent body 3 to be arranged along the gluteal cleft serving as a groove in the vicinity of the body excretory opening.

Temporary fixing portions 5 are formed in the top absorbent body 3. The temporary fixing portions 5 temporarily join the top absorbent body 3 to the base absorbent body 2 so as to be spaced apart therefrom with a predetermined force. The movement of the top absorbent body 3 is regulated top absorbent body in a state of being temporarily joined by the temporary fixing portions 5, while the movement thereof is not regulated in a state in which the temporary joining is released. The top absorbent body 3 is separated from the base absorbent body 2 with the fixing portion 4 as a starting point in a state where the temporary joining by the temporary fixing portions 5 is released.

Furthermore, the top absorbent body 3 includes a locking portion 37 at a position thereof on the side of the handle portion 40 near the free end 31 in the longitudinal direction LD. The locking portion 37 is arranged on a surface, opposed to the base absorbent body 2, of the top absorbent body 3, and is covered by the base absorbent body 2 with the top absorbent body 3 not spaced apart from the base absorbent body 2, while being exposed with the top absorbent body 3 spaced apart from the base absorbent body 2. That is, the locking portion 37 is protected by the base absorbent body 2 before the top absorbent body 3 is separated from the base absorbent body 2. The locking portion 37, after a state in which the position thereof is adjusted such that the top absorbent body 3 is separated from the base absorbent body 2 to extend along the gluteal cleft, locks the top absorbent body 3 to the base absorbent body 2 in order to maintain the state.

The top absorbent body 3 is arranged so as to be spaced apart from the base absorbent body 2 with the fixing portion 4 as a starting point. That is, the top absorbent body 3 can be manipulated (moved or deformed) independently of the base absorbent body 2. This allows the base absorbent body 2 to continue to fit tightly to the wearer's body without being affected by the movement of a garment on which the base absorbent body 2 is arranged. Each constituent element will be described in detail below.

1.2. Top Absorbent Body

As shown in FIGS. 1 to 11, the top absorbent body 3 is an absorbent core of substantially vertically-long shape arranged on the skin contacting side in the base absorbent body 2. More specifically, the top absorbent body 3 can be arranged along the central portion 20 in the base absorbent body 2, and includes a top absorbing portion 30 having an absorbent core 35 and a handle portion 40 in a substantially plate shape arranged on the side of the free end 31. The fixing portion 4 fixes one end portion in the longitudinal direction LD of the top absorbent body 3. Then, the end portion that is not fixed becomes the free end 31. An end portion on the side of the free end 31 of the top absorbing portion 30 is a free end portion 32. The fixing portion 4 can be formed at any position in the longitudinal direction LD of the top absorbent body 3. In the present embodiment, when the top absorbent body 3 is arranged on the base absorbent body 2, however, the fixing portion 4 is formed at a position, on the side of one end arranged on the side of a front edge 220, of the top absorbent body 3. The other end arranged on the side of a rear edge 230 is the free end 31.

As shown in FIG. 4, the free end 31 can be spaced apart from the base absorbent body 2. The top absorbent body 3 is adapted so that the free end 31 can be spaced apart from the base absorbent body 2 with the fixing portion 4 as a starting point from a state where it is arranged substantially at the center in the width direction WD of the central portion 20 in the base absorbent body 2. The free end 31 is an end portion far from the fixing portion 4, and the degree of freedom of the top absorbent body 3 becomes higher with a longer distance from the free end portion 32 to the fixing portion 4 body.

The free end 31 is formed at a position a predetermined distance apart from the fixing portion 4. Therefore, the position of the top absorbent body 3 in a worn state can be suitably adjusted by adjusting the position of the free end 31.

The top absorbent body 3 is arranged in a state where it extends 5 mm ahead of the front edge 220 in the base absorbent body 2 and 20 mm behind the rear edge 230 therein. The state extended 5 mm from the front edge 220 is provided in consideration of misalignment due to an error in manufacturing. Extending the top absorbent body 3 20 mm behind the rear edge 230 allows the handle portion 40 to be easily gripped when the handle portion 40 is gripped to pull up the free end 31 in the top absorbent body 3. Furthermore, the handle portion 40 can be formed in an extended portion.

As shown in FIGS. 3A, 3B, 3C, and 4, the top absorbing portion 30 includes a top layer 33 arranged on the skin contacting side, an absorbent core 35, and a back sheet 34 serving as a leakage-proof layer arranged on the base absorbent body 2 contacting side in the top absorbing portion 30. The top absorbing portion 30 is a principal member that absorbs a predetermined liquid excreted from the excretory opening.

The top layer 33 is formed by performing a perforation process a top sheet 331 and a second sheet 332 that are arranged to be layered. The top layer 33 has a plurality of openings formed therein by the abovementioned perforation process and is formed by integrating the top sheet 331 and the second sheet 332. The second sheet 332 is arranged so as to cover a surface, on the skin contacting side, of the absorbent core 35.

The top sheet 331 is arranged on the skin contacting side in the second sheet 332, and is arranged so as to wrap the whole of the second sheet 332, the absorbent core 355, described later, and the back sheet 34. The top sheet 331 forms an outermost surface of the top absorbing portion 30. The top sheet 331 is doubly arranged on the base absorbent body 2 contacting side in the top absorbing portion 30. It should be noted that the same member as the top sheet 27 in the base absorbent body 2, described later, can be used for the top sheet 331.

As shown in FIGS. 3A and 4, an end portion, on the side of the anterior region FA in the longitudinal direction LD, of the top absorbing portion 30 is in a state where only the top sheet 331 is triple-layered. The fixing portion 4 fixed to the base absorbent body 2 is arranged at the end portion on the side of the anterior region FA. It should be noted that it is preferable in a portion where the top sheet 331 is triple-layered, for layers to be bonded to one another with hot melt adhesives.

As shown in FIGS. 3C and 4, an end portion on the side of the posterior region BA in the longitudinal direction LD, of the top absorbing portion 30 is in a state where the top sheet 331 and the back sheet 34 are folded in three with the sheets layered and arranged to be triple-layered. Additionally, the handle portion 40, described later, is arranged at the end portion on the side of the posterior region BA. In addition, layers of each of the top sheet 331 and the back sheet 34 that are arranged to be layered are bonded to one another with hot melt adhesives at the end portion on the side of the posterior region BA.

The second sheet 332 is arranged on the skin contacting side in the top absorbing portion 30 so as to cover a top surface of the absorbent core 35, described later. In addition, the second sheet 332 is arranged to be layered between the top sheet 331 and the absorbent core 35, described later.

It is preferable for the second sheet 332 to be formed so as to be slightly larger than the absorbent core 35. In the present embodiment, the length in the longitudinal direction LD of the second sheet 332 is 300 mm, and the length thereof in the width direction WD is 45 mm.

The second sheet 332 according to the present embodiment is formed of a through-air non-woven fabric composed of a fiber having a core-sheath structure using polypropylene as a core and polyethylene as a sheath, for example, and having a fineness of 3.3 dtex and a length of 51 mm. Furthermore, the basis weight of the second sheet 332 is 20 g/m$^2$, for example. It is preferable that the second sheet 332 is formed such that the density thereof is higher than that of the top sheet 331. The second sheet 332 is higher in density than the top sheet 331, thereby allowing liquid migration from the top sheet 331 to be enhanced. In addition, a density gradient may be provided by not arranging the second sheet 332, but arranging the top sheet 331 one layer over the other.

Furthermore, as shown in FIGS. 3C and 4, the top absorbing portion 30 includes a back sheet 34 having liquid impermeability serving as a leakage-proof layer. The back sheet 34 is at least one portion, on the base absorbent body contacting side, of the absorbent core 35 and is arranged on the side of the rear edge 230.

It is preferable for the back sheet 34 to be arranged to a side surface of the absorbent core 35 from the base absorbent body contacting side and to not be arranged on the skin contacting side, as shown in FIG. 3C. This allows a predetermined liquid excreted in the top absorbing portion 30 to be absorbed in the absorbent core 35 when the liquid flows toward the rear edge 230. An SMS non-woven fabric having a basis weight of 24 g/m$^2$ and being composed of three layers, i.e., spunbond, meltblown, and spun bond layers formed of a film having liquid impermeability or a hydrophobic fiber, for example, can be used for the back sheet 34.

The absorbent core 35 mainly absorbs and holds the excreted predetermined liquid. The absorbent core 35 is formed of a ground pulp and a highly absorbent polymer. Here, it is preferable that the ground pulp is arranged such that the basis weight thereof partially differs in the top absorbing portion 30. More specifically, the basis weight of a region 353 where the fixing portion 4 is formed is 200 g/m², and the basis weight of regions 354, 355, and 356 from the fixing portion 4 to the free end portion 32 is 500 g/m², as shown in FIG. 5.

In addition, hollow portions 351 and 352 are formed in the posterior region BA in the top absorbing portion 30, as shown in FIG. 5. The hollow portion 351 is formed along the width direction WD on the side of the central region CA in the posterior region BA in the top absorbing portion 30, and the hollow portion 52 is formed along the width direction WD on the side of the rear edge 230 in the posterior region BA in the top absorbing portion 30.

The hollow portions 351 and 352 are regions where the weight of the ground pulp is lower than that in the other region. Additionally, the hollow portions 351 and 352 are folding starting points in a case where the absorbent article 1 is folded.

This inhibits, when the absorbent article 1 is folded when it is individually packed, for example, a wrinkle from appearing due to a difference in curvature between the inner side and the outer side of a fold.

Furthermore, a region 357 having a basis weight of 200 g/m² is formed in a vertically-long shape substantially at the center in the width direction WD of the top absorbing portion 30 in a region having a length of 80 mm directed toward the free end portion 32 from a position slightly closer to the free end portion 32 in relation to the position Z. The region 357 leads to deformation in the top absorbent body 3 in a worn state.

The absorbent core 35 is formed such that the length thereof in the longitudinal direction LD is less than the length in the longitudinal direction LD of the top sheet 331. That is, the absorbent core 35 is not arranged at both ends in the longitudinal direction LD of the top absorbing portion 30, as described above.

It is desirable for the length in the longitudinal direction LD of the top absorbent body 3 to be, for example, 200 mm to 500 mm, and preferably 230 mm to 450 mm. An example of the length in the longitudinal direction LD of the top absorbent body 3 in the first embodiment is 335 mm. In the present embodiment, an example of the length in the longitudinal direction LD of the top absorbing portion 30 is 280 mm.

In addition, in the present embodiment, the length in the width direction WD of the top absorbing portion 30 is less than the length in the width direction WD of the base absorbent body 2. Furthermore, it is preferable for the top absorbing portion 30 to have a length such that it can come into contact with the base absorbent body 2 in the longitudinal direction LD along the gluteal cleft.

More specifically, it is desirable for the length in the width direction WD of the top absorbing portion 30 to be 15 mm to 50 mm, and preferably 20 mm to 40 mm. In a case where the width dimension of the top absorbing portion 30 is less than 15 mm, the width is not sufficient for a napkin to maintain contact with the vaginal opening. Therefore, a clearance between the wearer's body and the napkin is liable to occur so that menstrual blood easily leaks. The width dimension of the top absorbing portion 30 according to the first embodiment can be exemplified, for example, as being made to 40 mm.

In addition, it is preferable for the top absorbing portion 30 to have a substantially equal width in the longitudinal direction LD. Furthermore, it is preferable for the cross-sectional shape in the width direction WD of the top absorbing portion 30 to be in a state where the skin contacting side and the base absorbent body 2 contacting side are at least substantially parallel to each other.

1.3. Fixing Portion

As shown in FIGS. 1 and 4, the fixing portion 4 is arranged at any position of the top absorbent body 3, to fix the top absorbent body 3 to the base absorbent body 2. More specifically, the top absorbent body 3 has a predetermined region thereof in the longitudinal direction fixed to the base absorbent body 2 by the fixing portion 4. In the top absorbent body 3, an end portion not fixed to the fixing portion 4 becomes a free end.

As shown in FIGS. 1 to 4, the fixing portion 4 is formed on the side of the front edge 220 in the top absorbent body 3 with the top absorbent body 3 placed on the base absorbent body 2. More specifically, the fixing portion 4 is formed at an end portion, on the side of the front edge 220, of the top absorbing portion 30 and a position corresponding to a region from a region formed of only the top sheet 331 to a region 353 having a basis weight of 200 g/m² of the absorbent core 35.

The fixing portion 4 is composed of a compression bonded portion 46 and a joining portion 47. The joining portion 47 is formed by substantially equally spacing hot melt adhesives along the longitudinal direction LD in a region formed of only the top sheet 331 in the top absorbent body 3 and a region where the absorbent core 35 is arranged, and placing the top absorbent body 3 substantially at the center in the width direction WD of the anterior region FA in the base absorbent body 2 to bond the base absorbent body 2 and the top absorbent body 3. It is preferable for the anterior region FA in the base absorbent body 2 to be coated with the hot melt adhesives so as to be opposed to a portion where the compressed grooves 22 are not arranged. In addition, a region from a predetermined position between the position Z and the front edge 220 to the front edge 220 is coated with the hot melt adhesives. That is, the fixing portion 4 is formed closer to the front edge 220 in relation to the position Z. It should be noted that the fixing portion 4 may be joined by integrating the top absorbent body 3 and the base absorbent body 2 not with hot melt adhesives, but by way of the compressed groove. In this case, a region where the base absorbent body 2 and the top absorbent body 3 are fixed to each other by the compressed groove is the fixing portion 4.

The compression bonded portion 46 is formed in a portion where the absorbent core 28 is not arranged on the side of the front edge 220 in the base absorbent body 2. The compression bonded portion 46 is formed in a region formed of only the top sheet 331 in the top absorbing portion 30 and the abovementioned portion of the base absorbent body 2.

The fixing portion 4 is joined by compression bonding for integrating the top layer 33 and the absorbent core 35 in the top absorbent body 3 with the base absorbent body 2.

1.4. Temporary Joining Portion

As shown in FIG. 1, temporary fixing portions 5 are formed in the top absorbent body 3. The temporary fixing portions 5 temporarily join the top absorbent body 3 to the base absorbent body 2 so as to be spaced apart from each other with a predetermined force. The movement of the top absorbent body 3 is regulated in a state in which the top absorbent body 3 temporarily joined by the temporary fixing portions 5, while the movement thereof is not regulated in a state in which the temporary joining is released. The top absorbent body 3 is spaced apart from the base absorbent body 2 with the fixing portion 4 as a starting point in a state where the temporary joining by the temporary fixing portions 5 is released. The temporary fixing portions 5 are formed between the fixing portion 4 and the free end portion 32 in the top absorbent body 3. In addition, in the base absorbent body 2, the temporary fixing portions 5 are formed in the vicinity of the rear edge 230 in the central portion 20.

More specifically, in the top absorbent body 3, the temporary fixing portions 5 are formed in the vicinity of the free end 31. More specifically, the temporary fixing portions 5 are formed on both sides in the width direction WD of the free end portion 32.

The temporary fixing portions 5 are formed in a region formed of only the top sheet 331 and the back sheet 34 in the top absorbent body 3. Furthermore, the temporary fixing portions 5 are formed in the vicinity of the handle portion 40 in the top absorbent body 3. A force exerted toward the outside in the longitudinal direction LD of the handle portion 40 or toward an upper surface in FIG. 1 is directly transmitted to the temporary fixing portions 5. In other words, when the handle portion 40 is moved outward in the longitudinal direction LD or toward the upper surface in FIG. 1, a temporarily joined state as for the temporary fixing portions 5 is released.

The temporary fixing portions 5 are respectively formed in a circular shape on both sides in the width direction WD of the free end portion 32 in the vicinity of the handle portion 40 in the top absorbent body 3, as described above. The top absorbent body 3 is fixed at points by the two temporary fixing portions 5, respectively.

In the base absorbent body 2, the temporary fixing portions 5 are formed on the side of the rear edge 230 in the base absorbent body 2. The temporary fixing portions 5 are formed in a region composed of only the top sheet 27 and the back sheet 29 in the base absorbent body 2.

The temporary fixing portions 5 are formed by performing an embossing process (compression bonding) from the upper surface of the top absorbent body 3 with the top absorbent body 3 arranged to be layered on the base absorbent body 2.

More specifically, the temporary fixing portions 5 are formed by compression-bonding the free end portion 32 formed of only the top sheet 331 and the back sheet 34 in the top absorbent body 3, and a region where the top sheet 27 and the back sheet 29 in the base absorbent body 2 are arranged to be layered while being heated by an embossing member having concavities and convexities formed on a top surface thereof. This causes the temporary fixing portions 5 that have been subjected to the embossing process to fix the top absorbent body 3 and the base absorbent body 2 by a mild degree of heat adhesion.

Here, a joining force of the temporary joining portions 5 is of such a degree that the free end 31 in the top absorbent body 3 and the base absorbent body 2 are not easily separated from each other in the process of putting onto the wearer's body. Furthermore, the joining force is of such a degree that the user can easily release the joining force without performing a complicated operation.

The locking portion 37 may also be used as the temporary fixing portions 5. That is, the locking portion 37 can function as the temporary fixing portions 5 by locking the locking portion 37 to the base absorbent body 2 before putting onto the wearer's body. That is, the movement of the free end 31 in the top absorbent body 3 can be regulated by locking the locking portion 37 serving as the temporary joining portions to the base absorbent body 2.

In addition, the locking portion 37 functioning as a temporary joining portion may be further arranged in addition to the abovementioned temporary joining portions 5 to achieve temporary joining by both the temporary joining portions 5 and the locking portion 37.

1.5. Handle Portion

As shown in FIGS. 1 and 4, the handle portion 40 is arranged on the side of the free end 31 in the longitudinal direction L of the top absorbing portion 30. The handle portion 40 is a portion pinched and pulled by the user to adjust the position of the top absorbent body 3 in the process of putting on the absorbent article 1. The handle portion 40 is formed so as to project most outwardly in the longitudinal direction LD at the center thereof in the width direction WD.

An outer edge of the handle portion 40 is in a curved shape. More specifically, the handle portion 40 can be formed so as to have a substantially semicircular shape taking an intersection of an extension substantially at the center in the width direction WD of the top absorbent body 3 and the outer edge as an apex.

The handle portion 40 is arranged on the side of the free end 31, and is formed in a region, on the side of the free end 31, of the top absorbing portion 30, where no absorbent core 35 exists and only the top sheet 331 and the back sheet 34 extend.

The handle portion 40 is formed by enhancing the rigidity of the free end portion 32 in the top absorbing portion 30. More specifically, the handle portion 40 is formed by subjecting a region, on the side of the free end portion 32, of the top absorbing portion 30, where only the top sheet 331 and the back sheet 34 extend, to the embossing process in order to enhance the rigidity thereof. The handle portion 40 has an embossed portion in the shape of a small circle formed in a gourd shape and has a flower-shaped embossed portion formed on its side portion. The embossed portion formed in a gourd shape functions as an element for guiding a position on which the user places his/her fingers in gripping the handle portion 40. An elaborately designed handle portion 40 can be provided by devising the shape of the embossed portion. That is, a guiding element and a pattern can be formed in the handle portion 40 by the embossing process for providing rigidity. That is, a predetermined function and custom design can be provided at one time in the process of providing rigidity.

Any design (guiding element) can be provided to the handle portion 40 depending on the shape of the embossed portion. For example, a display such as to suggest the handle portion 40 to be pinched and pulled in a predetermined direction in the longitudinal direction LD can be provided. More specifically, an arrow directed outward in the longitudinal direction LD so implied as to pull the handle portion 40 in the longitudinal direction LD, a point indicating a position to be pinched, and a predetermined color may be combined.

In addition, the handle portion 40 has concavities and convexities formed on the top surface thereof by being subjected to the embossing process. The convexities and concavities can provide an indication in searching for the handle portion 40 arranged at a position which cannot be seen from the user in the process of putting on the absorbent article 1.

The temporary fixing portions 5 are formed, as described above, in the vicinity of the handle portion 40. Since the temporary fixing portions 5 are respectively formed at positions following the movement of the handle portion 40, a temporarily joined state by the temporary fixing portions 5 is released by moving the handle portion 40 by a predetermined distance. More specifically, the temporarily joined state by the temporary fixing portions 5 is released by moving the handle portion 40 in order to lock the locking portion 37, described later, to the other position.

In addition, the locking portion 37, described later, is arranged in the vicinity of the handle portion 40. The locking portion 37 is arranged at a position following the movement of the handle portion 40. In other words, the handle portion 40 is arranged at a position where the movement (position) of the locking portion 37 can be suitably adjusted.

It is preferable for the outer edge of the handle portion 40 to extend from the rear edge 230 in the base absorbent body 2. More specifically, a range directed outward by 100 mm and directed inward by 50 mm, preferably directed outward by 60 mm and directed inward by 30 mm, and more preferably directed outward by 30 mm and directed inward by 20 mm can be exemplified for the rear edge 230 in the base absorbent body 2 as a starting point. The outer edge of the handle portion 40 extends from the rear edge 230 in the base absorbent body 2 so that it is easy for the user to grip the handle portion 40. For example, when the user searches for the handle portion 40 behind his/her back when wearing the absorbent article 1, the handle portion 40 is easy to identify. In addition, a portion projecting outward from the rear edge 230 in the handle portion 40 functions suitably as a gripping portion.

The flexural rigidity (B) of the handle portion 40 is 0.1 to 1.2 ($10^{-4}$N·m$^2$/m), preferably 0.2 to 1 ($10^{-4}$N·m$^2$/m), and more preferably 0.3 to 0.8 ($10^{-4}$N·m$^2$/m). When the flexural rigidity (B) of the handle portion 40 is less than 0.1 ($10^{-4}$N·m$^2$/m), a predetermined operation of gripping the handle portion 40 to arrange a top absorbent body in a predetermined area in the wearer's body, for example, may be difficult to perform in some cases. Conversely, in a case where the flexural rigidity (B) of the handle portion 40 is greater than 10, the handle portion 40 may, in some cases, give an uncomfortable feeling during wearing, for example. It is preferable for the flexural rigidity (B) of the handle portion 40 to be in the abovementioned range.

The flexure recovery (2HB) of the handle portion 40 is not more than 10 ($10^{-2}$ N·m/m), preferably not more than 7, and more preferably not more than 3 ($10^{-2}$ Nm/m). When the flexure recovery (2 HB) of the handle portion 40 is greater than ($10^{-2}$N·m/m), folds are easily formed when the handle portion 40 may be folded back halfway and, in some cases, give an uncomfortable feeling. Therefore, it is preferable for the flexure recovery (2HB) of the handle portion 40 to be in the abovementioned range.

It is preferable for the thickness of the handle portion 40 to be 0.5 mm to 4 mm, and preferably 0.7 to 3.5 mm. In a case where the thickness of the handle portion 40 is less than 0.5 mm, a user may worry that the handle portion may be torn when the user grips and pulls the handle portion 40. Conversely, in a case where the handle portion 40 is more than 5 mm, the user may feel a foreign-body sensation during use.

Measuring Method

The methods for measuring the flexural rigidity (B) and the recovery (hysteresis: 2 HB) of the handle portion 40 in the present invention will be described below, respectively.

The measuring device used was an Automatic Pure Bending Tester (Trade Name, Type Name "KESFB2-AUTO-A") manufactured by KATO TECH CO., LTD. Test samples having respective sizes adjusted to 100 mm×100 mm (when the widths thereof are insufficient, they were adjusted on a 10 mm basis between 10 mm to 100 mm) were used.

The relationship between a curvature and a bending moment was evaluated in a case where the test sample is returned to its original shape after being curved toward its front side to a maximum curvature of 2.5 cm$^{-1}$ by such pure bending so that a circular arc is always kept and is then returned to its original shape after being curved toward its back side to a maximum curvature of −2.5 cm$^{-1}$.

The flexural rigidity (B) is obtained as a value on a predetermined hysteresis curve, and is represented by an average slope between a curvature of 0.5 and a curvature of 1.5 cm$^{-1}$.

The flexure recovery (2 HB) is represented by a hysteresis width of a bending moment M in a curvature of 1.-cm$^{-1}$. This indicates that the higher flexure recovery (2 HB) is the worse (the lower) flexure recovery.

1.6. Locking Portion

As shown in FIGS. 1 to 4, the absorbent article 1 includes the locking portion 37 serving as a top absorbent body side locking portion and the central portion 20, serving as a base absorbent body side portion to be locked, in the base absorbent body 2 as a locking means. The locking portion 37 locks a part thereof on the side of the free end 31 in the top absorbent body 3 to a predetermined position. More specifically, the locking portion 37 locks the part thereof on the side of the free end 31 in the top absorbent body 3 to a predetermined position with the absorbent article worn on the wearer's body, which is a target for application. In detail, in the absorbent article 1, the base absorbent body 2 and the top absorbent body 3 can be locked to each other such that the free end 31 is arranged closer to the outer edge in the longitudinal direction LD of the base absorbent body 2 in relation to a position in a case where the base absorbent body 2 and the top absorbent body 3 are formed in a substantially planar shape.

A position to which the locking portion 37 is locked is a position closer to the outer edge in relation to a position with which the locking portion 37 comes into contact in a case where the top absorbent body 3 and the base absorbent body 2 are placed on a substantially planar surface. In other words, the locking portion 37 in the top absorbent body 3 is locked closer to the rear edge 230 in relation to a position of the locking portion 37 in a case where the top absorbent body 3 and the base absorbent body 2 are placed on a substantially planar. In this case, a position, to which a locking member is locked, in the base absorbent body 2 is a position closer to the outer edge (the rear edge 230) by not less than 2%, preferably not less than 5%, and more preferably not less than 8% of the length in the longitudinal direction LD of the base absorbent body 2 in relation to the position with which the locking portion 37 comes into contact when the top absorbent body 3 and the base absorbent body 2 are disposed to be substantially planar. According to this, suitable tension to be generated between the fixing portion 4 and the locking portion 37 in the top absorbent body 3.

The locking portion 37 is arranged on the side of the free end 31 in the top absorbent body 3. The locking portion 37 is arranged inside an outer edge in the longitudinal direction of the base absorbent body 2 when the base absorbent body 2 and the top absorbent body 3 are formed in a substantially planar shape. More specifically, the locking portion 37 is arranged on the side of the base absorbent body 2 in the top absorbent body 3 and in the posterior region BA.

In detail, the locking portion 37 is arranged substantially at the center in the width direction WD in the top absorbing portion 30. In addition, the locking portion 37 is arranged on the base absorbent body 2 contacting side in the top absorbent body 3 and at a position corresponding to a region between the nondense portion 351 in the absorbent core 35 and the hollow portion 352 arranged in the posterior region BA. In other words, the locking portion 37 is arranged on the base absorbent body 2 contacting side in the top absorbent body 3 and at a position corresponding to the region 355 in the absorbent core 35. More specifically, the locking portion 37 is arranged such that an end thereof on the side of the rear edge 230 corresponds to a position closer to an end, on the side of the front edge 220, of the hollow portion 352.

The locking portion 37 is arranged on a position, opposed to the base absorbent body 2, of the top absorbent body 3, and is in a protective state where it is coated with the base absorbent body 2 with the top absorbent body 3 not spaced apart from the base absorbent body 2, while entering a state where it is exposed to prepare locking to a member to be locked with the top absorbent body 3 spaced apart from the base absorbent body 2.

Providing the locking portion 37 at a position, which can be opposed to the base absorbent body 2, of the top absorbent body 3 produces the following effect. The locking portion 37 is not exposed to an outer surface with the top absorbent body 3 not spaced apart from the base absorbent body 2. This can inhibit the user, for example, from coming into contact with the locking portion 37. That is, unless the user attempts to intentionally come into contact with the locking portion 37, the hand of the user and the locking portion 37 rarely come into contact with each other. Therefore, the locking portion 37 is superior in sanitation, thereby eliminating the possibility of a locking force thereof being degraded by contact with the hand. In addition, the locking portion 37 enters a stage of preparing for locking to a member to be locked under an operation of pinching the handle portion to separate the top absorbent body 3 from the base absorbent body 2. Therefore, the locking portion 37 is superior in a sequence of operability, while being able to inhibit the user from coming into contact with the locking portion 37 even in an operating state.

Thus, applying a hook material to the locking portion 37 more significantly inhibits the locking force from being degraded, as compared with that in applying a pressure sensitive adhesive tape and a pressure sensitive adhesive as a locking member. If the hand of the user comes into contact with the locking portion 37 in the process of putting on so that grease from the hand adheres thereto, for example, the locking force is not weakened. Even if the hand of the user unnecessarily comes into contact with underwear or the like in the process of putting on, the locking force is not weakened. Therefore, the locking portion 37 can continue to function as a locking member for a long time.

Examples of a member forming the locking portion 37 include a pressure sensitive adhesive and a mechanical locking member. Examples of the pressure sensitive adhesive include seals coated with hot melt adhesives and a gel pressure sensitive adhesive. Examples of the mechanical locking member include a hook material serving as a male material used for a hook and loop fastener.

When the locking portion 37 is composed of a hook material, the male material used for the hook and loop fastener can be employed. More specifically, it is possible to use a hook material including a locking pin having a so-called mushroom shape or a hook material having directional properties. In the present embodiment, it is preferable for a hook material having directional properties to be used. Here, the hook material having directional properties is a hook material including a plurality of pins engaged with a fiber having predetermined directional properties. In detail, the hook material having directional properties is a hook material including a plurality of pins fixed to its base material with the pins inclined at a predetermined angle.

The hook material having directional properties is pressed against and engaged with a member to be locked. Movement of the hook material in the direction in which the pins are inclined is regulated, while the movement thereof in the opposite direction to the direction in which the pins are inclined is not regulated. That is, the hook material is not moved when pulled in the direction in which the pins are inclined as a predetermined direction, while being moved because the engagement is released when it moves parallel to the opposite direction to the direction in which the pins are inclined as a predetermined direction.

In a case where the hook material having directional properties is used as the locking portion 37, the hook material is arranged such that the plurality of pins are inclined in a direction toward the fixing portion 4 in the top absorbent body 3. Therefore, when the top absorbent body 3 and the locking portion 37 are brought into contact with the base absorbent body 2, the locking portion 37 is pulled in the direction in which the pins are inclined by tension generated by the curvature of the base absorbent body 2, thereby locking the locking portion 37 so that the movement thereof is regulated. In addition, when the top absorbent body 3 is pulled outward, since the locking portion 37 is pulled in the opposite direction to the direction in which the pins are inclined, the locking is released so that the locking portion 37 is moved.

It should be noted that it is preferable for the locking force of the locking portion 37 to not be weakened even if the absorbent article 1 is attached and detached a plurality of numbers of times. A member to be locked suitable for a member used for the locking portion 37 may be arranged in a region with which the locking portion 37 is intended to come into contact in the base absorbent body 2. This can prevent the locking force from being reduced by attaching and detaching the locking portion 37 a numerous times. When a pressure sensitive adhesive is used for the locking portion 37, for example, a mould releasing film can be arranged. Bringing the locking portion 37 into contact with the mould releasing film before wearing can prevent adhesive strength from being reduced because of fibers or the like adhering to the locking portion 37.

In addition, in a case where the hook material is used for the locking portion 37, a female material of the hook material, for example, can be arranged in a region with which the locking portion 37 is intended to come into contact in the base absorbent body 2 before wearing on the wearer's body or a region with which the locking portion 37 is intended to come into contact after putting on. Even if the absorbent article 1 is attached and detached a numerous times, the locking force of the hook material is slightly weakened; however, when the locking is released, pins composing the hook material may come off or fibers in a portion with which the hook material comes into contact may be damaged. Arranging the male material of the hook material in the region with which the locking portion 37 comes into contact before the absorbent article 1 is worn can prevent the pins composing the hook material from coming off or prevent fibers in the portion with which the hook material comes into contact from being damaged.

The locking portion 37 can also be used as the temporary fixing portions 5. In detail, the locking portion 37 can also be used as the temporary fixing portions 5 by previously locking the locking portion 37 to the base absorbent body 2 without forming the temporary fixing portions 5. In such a case, it is preferable for a hook material having directional properties to be used for a member composing the locking portion 37. It is possible to release the locking easily and without damaging the member to be locked and to prevent the locking force from being reduced even when the locking portion 37 is locked again. In addition, the necessity of the process of forming the temporary fixing portions 5 is eliminated at the time of manufacturing, which contributes to cost reduction.

1.7. Base Absorbent Body

The base absorbent body 2 is formed in a substantially rectangular shape, and includes the top sheet 27 having liquid permeability, the back sheet 29 having liquid impermeability, and the absorbent core 28 having liquid retention properties arranged between the top sheet 27 and the back sheet 29, as shown in FIG. 1 and FIGS. 3A, 3B, and 3C, and FIG. 4. In the base absorbent body 2, the strip-shaped central portion 20 is formed along the longitudinal direction LD substantially at the center in the width direction WD in the base absorbent body 2. The top absorbent body 3 is arranged in the central portion 20. In addition, gathers 21A and 21B are formed on both sides in the width direction WD of the central portion 20. The gathers 21A and 21B come into contact with the groin region to inhibit menstrual blood or the like flowing down the surface of the wearer's body without being absorbed in the top absorbent body 3 from leaking out. In addition, wings 23A and 23B are formed so as to project outward in the width direction WD on both sides, respectively, in the width direction WD in the absorbent article 1.

As shown in FIG. 2, in addition, the base absorbent body 2 has a dislocation preventing portion 26 arranged nearly at the center in the width direction WD on a back surface thereof serving as the another surface. Wing-side dislocation preventing portions 25A and 25B are arranged on back surfaces of the wings 23A and 23B, respectively.

The central portion 20 is formed in a strip shape along the longitudinal direction LD substantially at the center in the width direction WD of the base absorbent body 2. The central portion 20 is a thick region composing a base absorbing layer. The central portion 20 includes the top sheet 27, the back sheet 29, and the absorbent core 28. The top sheet 27 and the absorbent core 28 are respectively bonded with hot melt adhesives, and are joined to each other by a plurality of compressed grooves 22 formed along the longitudinal direction LD.

In the present embodiment, the top sheet 27 in the central portion 20 is formed of a through-air non-woven fabric having a basis weight of 30 g/m$^2$. In addition, the non-woven fabric is formed of a fiber using polypropylene as a core and polyethylene as a sheath and having a fineness of 2 dtex and a length of 51 mm. It should be noted that this fiber is preferably a fiber having a surface coated with a hydrophobic oil solution.

The absorbent core 28 is formed by layering a ground pulp having a highly absorbent polymer mixed therein and wrapping an obtained layered composition in a tissue (not shown). An example of the tissue is one having a basis weight of 15 g/m$^2$. It is preferable that the ground pulp is arranged such that the basis weight thereof differs from place to place in the central portion 20, as shown in FIG. 6. In a region 201 at a peripheral edge including the position Z, for example, the ground pulp can be layered such that the basis weight thereof is 500 g/m$^2$. In regions 202 in both side portions in the longitudinal direction LD of the region 201, the ground pulp is layered such that the basis weight thereof is 100 g/m$^2$. Furthermore, in a region 203 formed closer to the rear edge 230 in relation to the region 201 and along the longitudinal direction LD, the ground pulp is also layered such that the basis weight thereof is 100 g/m$^2$. A region 204 where the ground pulp has a basis weight of 300 g/m$^2$ is formed closer to the front edge 220 in the longitudinal direction LD in relation to the region 201. In the other region 205, the ground pulp can be arranged to be layered such that the basis weight thereof is 200 g/m$^2$. Although the highly absorbent polymer is mixed such that the average basis weight of the whole absorbent core 28 is 10 g/m$^2$, it is dispersed and arranged in proportion to the basis weight of the ground pulp in each of portions in the absorbent core 28. The reason for this is that the highly absorbent polymer and the ground pulp are uniformly dispersed.

As shown in FIG. 7, compressed grooves 22 are formed in the central portion 20. The compressed grooves 22 are formed by alternately arranging high compressed portions and low compressed portions in the longitudinal direction LD. In addition, the compressed grooves 22 are formed from the anterior region FA to the posterior region BA in the central portion 20. An example of the length in the width direction WD of the compressed grooves 22 is 2 mm. An example of spacing in the width direction WD between the adjacent compressed grooves 22 is 4 mm.

As shown in FIG. 7, six compressed grooves are formed in the anterior region FA. Compressed grooves 223, described later, are formed on the outer sides of the central portion 20 in the width direction WD. The compressed grooves 223 will be described later. Compressed grooves 221 are formed inside the compressed grooves 223 in the width direction WD, respectively. The compressed grooves 221 are formed from the anterior region FA to the posterior region BA and are connected to each other in the posterior region BA. The compressed grooves 221 continuously form a U-shaped compressed groove projecting toward the rear edge 230. Compressed grooves 222 are formed inside the compressed grooves 221, respectively, in the width direction WD. The compressed grooves 222 are formed in a linear shape from the anterior region FA to the central region CA.

In the central region CA, ends of a compressed groove 224, described later, are formed in addition to the above-mentioned six compressed grooves 221, 222, and 223. The compressed grooves 223 are formed from the anterior region FA to the central region CA and are formed in a gently curved shape projecting inward in the width direction WD. The compressed grooves 223 are formed such that spacing therebetween is the narrowest at a position corresponding to the position Z in the longitudinal direction LD. At this position, the abovementioned six compressed grooves 221, 222, and 223 are substantially equally spaced in the width direction WD. The compressed groove 224 will be described later.

In the posterior region BA, the compressed groove 224, a compressed groove 226, and compressed grooves 227 are formed in addition to the compressed grooves 221 continuously formed from the anterior region FA.

The compressed groove 224 is formed outside the compressed grooves 221. More specifically, the compressed groove 224 is formed so as to enclose the compressed grooves 221 formed in a U shape.

The compressed groove 226 is formed so as to extend in the width direction WD inside the compressed grooves 221. More specifically, the compressed groove 226 is formed so as to connect the compressed grooves 221 spaced apart from each other in the width direction WD on the side of the central region CA in the posterior region BA. The compressed groove 226 is formed such that the curve thereof projecting toward the rear edge 230 in the longitudinal direction LD has a gentle U shape.

The compressed grooves 227 are formed so as to extend in the longitudinal direction LD in a region enclosed by the compressed grooves 221 and the compressed groove 226.

In the posterior region BA, the three compressed grooves are formed so as to cross the region in the width direction WD. In other words, the three compressed grooves are formed in the longitudinal direction LD at the center in the width direction WD.

The compressed grooves 22 are integrally formed by compressing the absorbent core 28 and the top sheet 27, thereby imparting the central portion 20 with a predetermined rigidity. A relationship with the rigidity of the top absorbent body 3 can prevent the top absorbent body 3 from being dislocated when the absorbent article 1 is fixed to underwear and is pulled up. That is, it is possible to prevent situations where the top absorbent body 3 is dislocated because the top absorbent body 3 cannot follow the curvature of the base absorbent body 2 when the rigidity of the base absorbent body 2 is much lower than the rigidity of the top absorbent body 3.

As shown in FIGS. 1, 3A, 3B, and 3C, the gathers 21A and 21B are arranged along the longitudinal direction LD on both sides of the central portion 20. The gathers 21A and 21B are formed such that at least a portion thereof is raised in the thickness direction.

The gathers 21A and 21B in the present embodiment are respectively arranged along the longitudinal direction LD at positions spaced approximately 64 mm apart from the center in the width direction WD of the central portion 20. The gathers 21A and 21B are fixed at their respective root portions and respectively have ends 215A and 215B that are movable in the thickness direction. In a worn state, the ends 215A and 215B come into contact with the groin in the wearer's body.

The gathers 21A and 21B are portions obtained by folding a non-woven fabric of predetermined size that is more hydrophobic than the top sheet 27 in the central portion 20 into two for lamination. Elastic stretchable members 213A and 213B are arranged inside the folded non-woven fabric.

In the present embodiment, three elastic stretchable members 213A and 213B are substantially equally spaced. The elastic stretchable members 213A and 213B are formed of rubber threads having a fineness of 470 dtex, for example, and are fixed in a state where they are extended by approximately 1.3 times. The gathers 21A and 21B can be raised with such a force that the elastic stretch members 213A and 213B expand and contract.

Both ends in the longitudinal direction LD of each of the gathers 21A and 21B are folded outward in the width direction WD, and the ends are respectively fixed with hot melt adhesives 214A, 214B, 214C, and 214D. Then, the ends on the inner side in the longitudinal direction LD of the hot melt adhesives 214A, 214B, 214C, and 214D are respectively feet of the gathers 21A and 21B, and a region between the feet is a portion that is raised during use.

In addition, the gathers 21A and 21B in the present embodiment can be formed of a spunbond non-woven fabric formed of a fiber using polypropylene as a core and polyethylene as a sheath and having a basis weight of 22 g/m$^2$.

The respective sizes of the gathers 21A and 21B can be changed, as needed, depending on the size of the base absorbent body 2. Although stresses in the elastic stretch members 213A and 213B can be determined by the thickness, the number, and the stretching enlargement ratio of rubber threads to be used, they can be changed, as needed, depending on the size of the base absorbent body 2. In this case, it is important to prevent a rough sensation of the gathers 21A and 21B when in contact with the skin.

The cross-sectional shape in the width direction WD of the gathers 21A and 21B is such that free ends of the gathers 21A and 21B are arranged so as to be directed outward in the width direction WD in the base absorbent body 2, as shown in FIG. 3B, in the first embodiment.

More specifically, by inwardly bending in the width direction WD the feet of the gathers 21A and 21B that are fixed, and by outwardly bending in the width direction WD a central portion in the longitudinal (height) direction of the gathers 21A and 21B, the end portions of the gathers 21A and 21B are disposed outward in the width direction WD. In the present embodiment, although the gathers 21A and 21B are folded back once, the present invention is not limited to the same. For example, the gathers 21A and 21B may be folded back three times to have a substantially sigma cross-sectional shape in which the free ends are directed outward in the width direction WD in the base absorbent body 2. In addition, the gathers 21A and 21B may be arranged with the free ends directed inward in the width direction WD in the base absorbent body 2.

It is preferable for raised starting points of the gathers 21A and 21B in the anterior region FA and an end, on the side of the rear edge, of the fixing portion 4 to be not at the same position in the longitudinal direction LD. More preferably, it is preferable for the end, on the side of the rear edge 230, of the fixing portion 4 to be arranged closer to the rear edge 230 in relation to the raised starting points of the gathers 21A and 21B. This is for preventing the two forces from being respectively applied to the same position, because the raised starting points of the gathers 21A and 21B are portions to which a force for expanding and contracting the elastic stretch members 213A and 213B is applied and the end, on the side of the rear edge 230, of the fixing portion 4 is a portion to which a force is applied when the top absorbent body 3 is separated from the base absorbent body 2.

In addition, the back sheet 29 having liquid impermeability can be arranged on a surface, on the opposite side to a surface on which the top absorbent body 3 is arranged, of the base absorbent body 2. Arranging the back sheet 29 having liquid impermeability can prevent a predetermined liquid that cannot be absorbed even by the base absorbent body 2 from adhering to underwear.

The wings 23A and 23B are respectively formed so as to project outward in the width direction WD on both sides in the width direction WD in the absorbent article 1. The wings 23A and 23B are composed of a non-woven fabric forming the back sheet 29 having liquid impermeability and the gathers 21A and 21B, and extend outward in the width direction WD in the base absorbent body 2. The back sheet 29 and the non-woven fabric are bonded to each other with hot melt adhesives. As shown in FIG. 2, the wings 23A and 23B have wing side dislocation preventing portions 25A and 25B on their surfaces on the underwear side, respectively. It is possible to fix the whole absorbent article 1 to the underwear by folding back the wings 23A and 23B toward the underwear and affixing the wing side dislocation preventing portions 25A and 25B to the underwear.

An example of the distance from the position Z to the front edge 220 on the front side in the longitudinal direction LD is 110 mm. In addition, an example of the distance from the position Z to the rear edge 230 is 220 mm.

Here, an example of the length in the width direction WD of the central portion 20 in the base absorbent body 2, excluding the length of the wings 23A and 23B, is 70 mm to 120 mm, and preferably 80 mm to 110 mm. In the present embodiment, an example of the length is 110 mm. It is desirable that the length in the width direction WD in the base absorbent body 2, including the length of the wings 23A and 23B, is 120 to 200 mm, and more preferably 140 to 180 mm. An example of the length in the width direction WD, including the length of the wings 23A and 23B, in the present embodiment is 160 mm. The length in the width direction WD in the base absorbent body 2 is preferably 1.5 to 7 times, and more preferably 2 to 5 times, the width of the top absorbing portion 30.

It is desirable for the length in the longitudinal direction LD of the base absorbent body 2 to be 250 to 500, and preferably 270 to 450 mm, for example. An example of the length in the longitudinal direction LD in the first embodiment is 330 mm. In addition, it is desirable for the length in the width direction of the base absorbent article 2, excluding the length of the wings 23A and 23B, to be 70 to 120 mm, and preferably 80 mm to 110 mm, for example.

The absorbent article 1 can be manufactured so as to include the following procedure, for example. First, in the base absorbent body 2, the top sheet 27 and the absorbent core 28 are arranged to be layered, and are subjected to compression bonding using an embossing roll in a predetermined pattern from the absorbent core 28, to form the compressed grooves 22 and compression-bond them to one another. Furthermore, the base absorbent body 2 is formed by arranging to be layered the back sheet 29 having liquid permeability on a surface, on the opposite side to the top sheet 27, of the absorbent core 28 and joining them with hot melt adhesives.

In addition, the top absorbent body 3 forms the top absorbing portion 30 in such a manner that the absorbent core 35 in a vertically-long shape, the second sheet 332, and the back sheet 34 are first arranged respectively at predetermined positions and are wrapped by the top sheet 331. A region where the absorbent core 35 is not arranged at one of both ends in the longitudinal direction LD is then embossed, to form the handle portion 40. The top absorbent body 3 and the base absorbent body 2 are joined to each other in such a manner that the other end is coated with hot melt adhesives and is laminated to the base absorbent body 2 in the anterior region FA. Thus, a region (a joining portion 47) where the top absorbent body 3 and the base absorbent body 2 are joined to each other and a compression bonded portion 46, described later, constitute the fixing portion 4, and an end, on the side on which the handle portion 40 is formed, of the top absorbent body 3 constitutes the free end 31.

In addition, a region where a region formed of only the top sheet 331 and the back sheet 34 on the side of the free end 31 in the top absorbent body 3 and a region formed of only the top sheet 27 and the back sheet 29 on the side of the rear edge 230 in the base absorbent body 2 are overlapped with each other is subjected to heat treatment by embossing, to form the temporary fixing portions 5. Additionally, a region where a region formed of only the top sheet 27 and the back sheet 29 on the side of the front edge 220 in the base absorbent body 2 and the top absorbent body 3 are overlapped with each other is also subjected to heat treatment by embossing, to fix the top absorbent body 3 to the base absorbent body 2.

1.8. Manner of Use

Referring to FIGS. 8 to 11, an example of a manner of use in the absorbent article 1 will be described.

First, as shown in FIG. 8, the absorbent article 1 is in a state where the top absorbent body 3 is placed on an upper surface of the base absorbent body 2. The top absorbent body 3 is arranged along the longitudinal direction LD in the central portion 20 in the base absorbent body 2. Furthermore, the top absorbent body 3 is temporarily joined to the base absorbent body 2 by the temporary fixing portions 5. The whole absorbent article 1 is deformable in an overall gentle U shape along a curvature in the vicinity of the excretory opening in the wearer's body.

As shown in FIG. 9, the absorbent article 1 is then arranged in a crotch area of underwear. Similarly to normal conventional absorbent article, the wings 23A and 23B are folded so as to wrap the underwear in the area where the absorbent article 1 is arranged. The absorbent article 1 is fixed to the underwear by the wing side dislocation preventing portions 25A and 25B arranged on the back surfaces of the wings 23A and 23B, respectively. The absorbent article 1, together with the underwear, is pulled up toward the wearer's body with the top absorbent article 3 arranged on the upper surface of the base absorbent article 2. Here, due to the top absorbent article 3 being temporarily joined by the temporary fixing portions 5, the top absorbent body 3 is not separated from the base absorbent body 2 until the temporary joining is released in the putting on process.

Then, the user inserts his/her hand into an area between the wearer's body and the underwear from behind the wearer's body, to grip the handle portion 40 to pull up the top absorbent body 3 in a direction indicated by an arrow R, as shown in FIG. 10.

In this way, since the temporary joining by the temporary fixing portions 5 is released, the top absorbent article 3 is separated from the base absorbent article 2. The locking portion 37 that has been so far protected is exposed to enter a stage of preparation of locking to a member to be locked. The top absorbent body 3 that has been spaced apart from the base absorbent body 2 is moved so as to enter the gluteal cleft with the fixing portion 4 as a starting point. That is, the top absorbent body 3 is separated from the base absorbent body 2 by pulling up the handle portion 40 gripped by the user. The top absorbent body 3 is moved so as to come into contact with the excretory opening and enter the gluteal cleft.

As shown in FIG. 11, the top absorbent body 3 arranged so as to enter the gluteal cleft is locked to the top surface of the base absorbent body 2 by the locking portion 37 arranged on the side of the free end. When a hook material is used for the locking portion 37, the top absorbent body 3 can be locked by performing such an operation as to press the locking portion 37 against the top surface of the base absorbent body 2. When the locking portion 37 is pressed against the top surface of the base absorbent body 2, a plurality of pins in the hook material composing the locking portion 37 are engaged with a fiber such as a non-woven fabric forming the base absorbent body 2. The top absorbent body 3 is brought into contact with the wearer's body with a predetermined tension exerted by the fixing portion 4 and the locking portion 37.

The position where the locking portion 37 is locked is closer to the rear edge 230 in relation to the position of the locking portion 37 in a case where the top absorbent body 3 and the base absorbent body 2 are formed in a substantially planar shape. In other words, the position of the portion to be locked in the base absorbent body 2 is closer to the outer edge (the rear edge 230) in the longitudinal direction in relation to the position of the locking portion 37 in a case where the top absorbent body 3 and the base absorbent body 2 are placed in a substantially planar shape.

In addition, the locking portion 37 can also be locked by only releasing the gripped handle portion 40. More specifically, when the gripped handle portion 40 is released, tension generated by the fixing portion 4 and the gripped handle potion 40 is released, and the top absorbent body 3 is pulled toward the front edge 220. At this time, due to the top absorbent body 3 being positioned between the underwear serving as a garment and the wearer's body, a surface, on the base absorbent body 2 contacting side, of the top absorbent body 3 slides on the top surface of the base absorbent body 2. This causes the locking portion 37 to also similarly slide toward the fixing portion 4 on the top surface of the base absorbent body 2 while being pressed by the wearer's body and the underwear. The locking portion 37 is locked by being pressed against the top surface of the base absorbent body 2. Furthermore, the use of the hook material having directional properties causes the movement of the locking portion 37 toward the fixing portion 4 to be regulated.

This causes the top absorbent body 3 to be maintained in a positional state adjusted by the user. More specifically, since the top absorbent body 3 is brought into contact with the wearer's body with a predetermined tension generated by the fixing portion 4 and the locking portion 37, a predetermined force is always exerted on the top absorbent body 3 in the direction in which the top absorbent body 3 comes into contact with the wearer's body. That is, the top absorbent body 3 is fixed such that a state where it comes into contact with the wearer's body is maintained.

Using the hook material having directional properties for the locking portion 37 allows, even after the top absorbent body 3 is locked, as described above, the position thereof to be adjusted again. That is, the locking of the top absorbent body 3 by the locking portion 37 is released only by the user gripping the handle portion 40 from behind the wearer's body and pulling the handle portion 40 toward the rear edge 230 in the base absorbent body 2, which allows the top absorbent body 3 to move. The top absorbent body 3 can be locked again in the same manner as described above after the position thereof is adjusted.

The back sheet 34 arranged on the base absorbent body contacting side in the top absorbent body 3 prevents menstrual blood absorbed by the top absorbent body 3 from leaking. When the top absorbent body 3 is locked, the free end portion 32 in the top absorbing portion 30 projects more outwardly than the rear edge 230 in the base absorbent body 2. Due to the back sheet 34 being arranged in a projected region, even if menstrual blood or the like runs down toward the free end portion 32 in the top absorbent body 3, the menstrual blood or the like is prevented from adhering to the underwear.

Here, the top absorbent body 3 arranged so as to come into contact with the excretory opening to enter the gluteal cleft is deformed along the shapes of the excretory opening and the gluteal cleft.

More specifically, the top absorbent body 35 in the top absorbent body 3 differs in basis weight from place to place where it is arranged. Therefore, a portion having a lower basis weight than a periphery thereof is used as a folding starting point so that the absorbent core 35 is deformed along the shapes of the excretory opening and the gluteal cleft. In detail, a region 357 formed closer to at the center in the width direction WD of the top absorbing portion 30 is arranged such that the basis weight of the absorbent core 35 is lower than that in the periphery thereof. As a result, as the top absorbent body 3 is arranged so as to enter the gluteal cleft with a portion of the region 357 becoming a fold starting point, it is deformed in a mound shape with the region 357 as an apex.

The region 357 is formed so as to correspond to a region from the perineal area to the anus of the wearer's body when the top absorbent body 3 is applied to the gluteal cleft. Therefore, it is formed such that the top absorbent body 3 enters the deepest part of the gluteal cleft. Since the top absorbent body 3 is thus deformed depending on the shape of the excretory opening or the like, as described above, the top absorbent body 3 is arranged so as to tightly fit the excretory opening or the like. The top absorbent body 3 is arranged with no clearance provided between the top absorbent body 3 and the wearer's body. That is, the top absorbent body 3 is so arranged that it comes into contact with the excretory opening to directly absorb menstrual blood or the like and can inhibit menstrual blood or the like from flowing down the surface of the wearer's body.

In addition, the base absorbent body 2 absorbs a predetermined liquid that cannot be absorbed only by the top absorbent body 3. The liquid that cannot be absorbed by the top absorbent body 3 is absorbed in the absorbent core 28 in the base absorbent body 2 through a portion where the top absorbent body 3 and the base absorbent body 2 come into contact with each other. The back sheet 29 having liquid impermeability prevents the predetermined liquid absorbed in the base absorbent body 2 from soaking into the underwear. The liquid is held in the absorbent core 28 in the base absorbent body 2.

Here, although a case where the absorbent article 1 is employed by spacing apart the top absorbent body 3 from the base absorbent body 2 has been described in the above, the absorbent article 1 can be also employed with the top absorbent body 3 not spaced apart from the base absorbent body 2. That is, the absorbent article 1 can be employed in the same manner as a conventional sanitary napkin without releasing the temporary joining by the temporary fixing portions 5. The user can choose which state is used to employ the absorbent article 1 at the time of putting on.

According to the present embodiment, due to the top absorbent body 3 being separated from the base absorbent body 2 with the fixing portion 4 taken as a starting point, the top absorbent body 3 can be operated independently of the base absorbent body 2. This causes the degree of freedom at which the top absorbent body 3 can move to be increased, allowing the absorbent body to continue to tightly fit the wearer's body without being affected by the movement of a garment on which the base absorbent body 2 is arranged.

According to the present embodiment, since the top absorbent body 3 and the base absorbent body 2 are fixed to each other by the fixing portion 4, the top absorbent body 3 and the base absorbent body 2 are not completely spaced apart from each other. As a result, in a case where the absorbent article 1 is removed from the wearer's body, the wearing of the top absorbent body 3 is released only by pulling down the underwear to which the base absorbent body 2 is fixed from the wearer's body.

According to the present embodiment, the top absorbent body 3 can be maintained at its position adjusted when put on by locking the locking portion 37 to the base absorbent body 2 when putting on. This allows a state where the top absorbent body 3 tightly fits the wearer's body to be maintained. Accordingly, it is possible to suitably absorb a liquid such as menstrual blood excreted from the excretory opening while inhibiting the liquid from flowing down the wearer's body to leak.

According to the present embodiment, since the locking portion 37 is locked to the top surface of the base absorbent body 2, a locking position and a locking object can be specified. Therefore, a locking member is easy to select. In addition, due to the locking object being able to be specified, a state where the locking portion 37 cannot be locked depending on the locking object can be avoided.

According to the present embodiment, the top absorbent body 3 differs in the basis weight of the absorbent core 35, thereby deforming with the basis weight difference as a starting point. More specifically, the top absorbent body 3 can be deformed along the shapes of the excretory opening and the gluteal cleft. The top absorbent body 3 can be deformed so as to tightly fit the excretory opening such as the vaginal opening. Particularly, a portion having a low basis weight is formed substantially at the center in the width direction WD of the top absorbing portion 30, which can inhibit the top absorbent body 3 from being so deformed as to be folded with a position that is not the center in the width direction WD used as a starting point. Furthermore, due to the portion having a low basis weight being formed at least from the perineum to the anus in the longitudinal direction, the top absorbent body 3 can be brought into contact with an inner part of the gluteal cleft which is desired to be tightly fit. This can inhibit the liquid from flowing down the wearer's body to leak.

According to the present embodiment, the temporary fixing portions 5 regulate the movement of the top absorbent body 3 until the temporary joining by the temporary fixing portions 5 is released. Since the top absorbent body 3 is fixed to a particular position when the user adjusts the position of the top absorbent body 3, the position of the handle portion 40 arranged at the end of the top absorbent body 3 is easy to grip.

According to the present embodiment, the temporary fixing portions 5 regulate the movement of the top absorbent body 3. As a result, two types of usage methods for the absorbent article 1 are provided. That is, as the first usage method, the top absorbent body 3 can tightly fit the gluteal cleft by releasing the temporary joining by the temporary fixing portions 5, to separate the free end 31 of the top absorbent body 3 from the base absorbent body 2. As the second usage method, the absorbent article 1 can be employed with the top absorbent body 3 temporarily joined to the base absorbent body 2 without releasing the temporary joining by the temporary fixing portions 5. Thus, the user can select the appropriate usage method for the absorbent article 1, as needed, on the spot. This eliminates the necessity of distinguishing among the uses of a plurality of types of absorbent articles, allowing a number of articles stored by the user to be reduced.

According to the present embodiment, the locking portion 37 is not exposed to an outer surface of the absorbent article 1 with the top absorbent body 3 not spaced apart from the base absorbent body 2, which can inhibit the user, for example, from coming into contact with the locking portion 37. In addition, since the handle portion 40 is arranged closer to the outer edge in the base absorbent body 2 in relation to the locking portion 37, the user can grip the handle portion 40 in a wearing operation. This can also inhibit the user from coming into contact with the locking portion 37 even during manipulating to put on. In addition, since the outer edge of the handle portion 40 is extended from the rear edge 230 in the base absorbent body 2, the user is led to grip the extended outer edge of the handle portion 40 while manipulating to put on. This can further inhibit the user from coming into contact with the locking portion 37 while manipulating to put on.

2. Other Embodiments

Second to fifth embodiments will be described with reference to FIGS. 13 to 15. The second to fifth embodiments are other embodiments with regards to locking means. It should be noted that, in the following embodiments, portions that are not particularly described are the same as those in the first embodiment, and the same portions as those in the first embodiment are assigned the same reference numerals in the drawings as those in the first embodiment.

2.1. Second Embodiment

As shown in FIGS. 12A and 12B, an absorbent article in the second embodiment differs from that in the first embodiment in the forms of a locking portion 37A and a portion to be locked. FIG. 12A is an enlarged plan view, on the side of a rear edge 230, of a base absorbent body 2A in the second embodiment. FIG. 12B is an enlarged back view, on the side of a free end 31, of a top absorbent body 3A in the second embodiment.

In the present embodiment, the locking portion 37A is formed in a substantially vertically-long shape, and is arranged along a width direction WD on the side of the free end 31 in the top absorbent body 3A, as shown in FIG. 12B. In detail, when the top absorbent body 3A and the base absorbent body 2A are formed in a substantially planar shape, the locking portion 37A is arranged along the width direction WD at a position, which does not come into contact with a engaging portion (or a portion to be locked) 8A, described later, and on the base absorbent body 2A contacting side in the top absorbent body 3A.

As shown in FIG. 12A, a engaging portion 8A serving as a base absorbent body portion to be locked is arranged on the side of the rear edge 230 in the base absorbent body 2. The engaging portion 8A has a length that is substantially identical to the length in the width direction WD of a central portion 20, and is fixed to the central portion 20 so as to cross the central portion 20 in the width direction WD. Both side portions, extending along a longitudinal direction LD, of the engaging portion 8A are not fixed to the central portion 20, and both ends thereof in the longitudinal direction LD are fixed to the central portion 20 so as to cross the central portion 20 in the width direction WD. Furthermore, a temporary joining sheet 81A is arranged adjacent to an inner side portion in the longitudinal direction LD of the engaging portion 8A in the base absorbent body 2A. The temporary joining sheet 81A is arranged in a region with which the locking portion 37A serving as a top absorbent body side locking portion comes into contact when the base absorbent body 2A and the top absorbent body 3A are formed in a substantially planar shape.

A member used for the engaging portion 8A can be optionally selected by a combination of a member forming the locking portion 37A. More specifically, in a case where the locking portion 37A is formed of a hook material, a known non-woven fabric and a surface material and a loop material that are the same as the top sheet 27 in the first embodiment can be exemplified for the member.

In addition, in a case where the locking portion 37A is formed of a hook material, the engaging portion 8A is preferably formed of a stretchable elastic member. In detail, it is desirable for the member to be a material having stretchability of 3% to 50%, and preferably 5% to 20%, of the distance from the fixing portion 4 to the locking portion 37A in the longitudinal direction LD in the base absorbent body 2A. Using such an elastic member causes the engaging portion 8A to serve as a buffer region that reduces a sense of pressure on the wearer's body and prevents the locking portion 37A from coming off the engaging portion 8A because the engaging portion 8A is stretched when the wearer's body or underwear moves while the absorbent article 1 is fixed.

In addition, it is preferable for the stretching enlargement ratio of the elastic member to be 1.05 to 3, preferably 1.1 to 2.5, and more preferably 1.2 to 2.0.

A non-woven fabric having stretchability, and a member on which a non-woven fabric is laminated such that a stretching member such as a rubber thread is sandwiched therebetween can be exemplified as the elastic member. In addition, for the non-woven fabric having stretchability, various materials such as a non-woven fabric formed of a fiber having stretchability can be used.

Alternatively, as an elastic member suitable for use for the engaging portion 8A, a stretchable non-woven fabric obtained by gear stretching can be given. More specifically, the engaging portion 8A can be formed of a spunbond non-woven fabric obtained by mixing a polyurethane long fiber and a polypropylene long fiber. For example, the elastic member can be obtained by subjecting a non-woven fabric having a polyurethane fiber and a polypropylene fiber mixed at a ratio of 50:50 and having a basis weight of 35 g/m$^2$ to gear stretching such that the stretching range thereof is doubled in the longitudinal direction LD.

When the locking portion 37A is formed of a pressure sensitive adhesive, an example of a member that can be used for the engaging portion 8A is a mould releasing film.

The temporary joining sheet 81A is formed of a member having a locking force that is made weaker than that in a case where the locking portion 37A is locked to the engaging portion 8A. The member to be used for the temporary joining sheet 81A can be selected from a suitable member complimenting the member used for the locking portion 37A.

An example of the member used for the temporary joining sheet 81A can be formed by a mould releasing film in a case where the locking portion 37A is formed of a pressure sensitive adhesive. In addition, in a case where the locking portion 37A is formed of a hook material, members made of a non-woven fabric and a non-woven fabric that has been subjected to such embossing as to smooth the top surface thereof can be exemplified for the temporary joining sheet 81A. Furthermore, when the locking portion 37A is formed of the above-mentioned hook material having directional properties, the temporary joining sheet 81A can be formed of the same non-woven fabric or loop material as that forms the top sheet 331 in the first embodiment. Here, the loop material is a member composed of a base material having a fiber fixed to the surface thereof so as to have a loop shape. More specifically, a male material of a hook and loop fastener can be exemplified.

In addition, the length, in the width direction WD of the base absorbent body 2A, of the engaging portion 8A is preferably 2 to 15 cm, and more preferably 3 to 8 cm. In a case where the length in the width direction WD of the engaging portion 8A is less than 2 cm, a region where the locking portion 37A can come into contact with the engaging portion 8 is reduced, so that the locking portion 37A cannot, in some cases, be locked when the absorbent article is worn. In addition, in a case where the length is not less than 15 cm, the width dimension of the base absorbent body 2A is exceeded.

Moreover, the length in the width direction WD of the engaging portion 8A is 2 cm to 15 cm, and preferably 3 cm to 8 cm. When the length is less than 2 cm, a region where the locking portion 37A can come into contact with the engaging portion 8A is reduced.

The length in the longitudinal direction LD and the length in the width direction WD of the temporary joining sheet 81A can be respectively made substantially identical to or more than the length in the longitudinal direction LD and/or the length in the width direction WD of the locking portion 37A. It is preferable for the temporary joining sheet 81A to be formed such that the locking portion 37A does not protrude from the temporary joining sheet 81A when the locking portion 37A comes into contact with the temporary joining sheet 81A.

In the present embodiment, although the base absorbent body 2A includes the temporary joining sheet 81A, the present invention is not limited thereto, and the base absorbent body 2A need not include the temporary joining sheet 81A. In a case where the locking portion 37A is formed of a hook material, it can be locked to a surface material of the base absorbent body 2A and temporarily joined thereto.

In addition, in the present embodiment, although different members are respectively used for the temporary joining sheet 81A and the engaging portion 8A, the present invention is not limited thereto. For example, in a case where the locking portion 37A is formed of a directional hook or a pressure sensitive adhesive, the same member can be used for the temporary joining sheet 81A and the engaging portion 8A.

2.2. Third Embodiment

As shown in FIGS. 13A and 13B, an absorbent article in the third embodiment differs from that in the first embodiment in the forms of a locking portion 37B and a engaging portion (or a portion to be locked) 8B. FIG. 13A is an enlarged plan view, on the side of a rear edge 230, of a base absorbent body 2B according to the third embodiment. FIG. 13B is an enlarged back view, on the side of a free end 31, of a top absorbent body 3B according to the third embodiment.

The locking portion 37B and an elastic member 82B are arranged in the base absorbent body 2B. More specifically, the elastic member 82B is, for example, arranged on the top absorbent body 3B contacting side in the base absorbent body 2B, and the locking portion 37B is arranged on the top absorbent body 3B contacting side in the elastic member 82B. The locking portion 37B is arranged so as to cross the elastic member 82B in a width direction WD substantially at the center in a longitudinal direction LD of the elastic member 82B.

The elastic member 82B has a length that is substantially identical to the length in the width direction WD of a central portion 20, and is fixed to the central portion 20 such that both ends in the longitudinal direction LD of the base absorbent body 2B cross the central portion 20 in the longitudinal direction LD. Additionally, both side portions extending along the longitudinal direction LD of the elastic member 82B are not fixed to the central portion 20, and both ends thereof in the longitudinal direction LD are fixed to the central portion 2D in the width direction WD.

Usable as a member for the elastic member 82B is the same elastic member as that for the engaging portion 8A in the second embodiment.

In addition, in the top absorbent body 3B, it is preferable for a temporary joining sheet 81B to be arranged in a region with which the locking portion 37B comes into contact in a case where the base absorbent body 2B and the top absorbent body 3B are formed in a substantially planar shape. In a state where an absorbent article 1B has not been employed yet, the locking portion 37B is locked to the temporary joining sheet 81B and is temporarily joined thereto.

It is preferable for the locking portion 37B to be formed in a substantially vertically-long shape of a hook material or the like. In detail, the same member as the hook material in the first embodiment can be used. Forming the locking portion 37B of a hook material allows, if a surface on the base absorbent body 2B contacting side of the top absorbent body 3B is formed of a non-woven fabric, the whole surface of the top absorbent body 3B can be made as the engaging portion 8B.

In the present embodiment, the locking portion 37B is a base absorbent body side locking portion, and a portion on the base absorbent body contacting side of the top absorbent body 3B is a top absorbent body side portion to be locked. A position where the locking portion 37B is locked is closer to an outer edge in the longitudinal direction LD in relation to a position of the locking portion 37B in a case where the top absorbent body 3B and the base absorbent body 2B are formed in a substantially planar shape.

2.3. Fourth Embodiment

As shown in FIGS. 14A and 14B, an absorbent article according to the fourth embodiment differs from that in the first embodiment in the forms of a locking portion 37C and an engaging portion 8C. FIG. 14A is an enlarged plan view, on the side of a rear edge 230, of a base absorbent body 2C according to the fourth embodiment. FIG. 14B is an enlarged back view, on the side of a free end 31, of a top absorbent body 3C according to the fourth embodiment.

As shown in FIG. 14B, the locking portion 37C is formed in a substantially vertically-long shape, and is arranged in the top absorbent body 3C. More specifically, the locking portion 37C is arranged on the base absorbent body contacting side in the top absorbent body 3C and along a longitudinal direction LD in the top absorbent body 3C. An elastic member 82C, more specifically, can be arranged between the locking portion 37C and the top absorbent body 3C. In detail, the elastic member 82C is arranged on the base absorbent body contacting side in the top absorbent body 3C, and the locking portion 37C serving as a top absorbent body side locking portion is arranged on the top absorbent body contacting side in the elastic member 82C.

The elastic member 82C has a length that is substantially identical to the length in a width direction WD of the top absorbent body 3C. The elastic member 82C is fixed along the width direction WD of the top absorbent body 3C, and both side portions thereof in the longitudinal direction LD are not fixed. Usable as a member forming the elastic member 82C is the same member as that forming the engaging portion 8A in the second embodiment.

It is preferable for a hook material to be used for a member forming the locking portion 37C. By using a hook material causes, if a surface on the top absorbent body 3C contacting side of the base absorbent body 2C is formed of a member that can be locked by a hook material such as a non-woven fabric, the whole surface on the top absorbent body 3C contacting side of the base absorbent body 2C becomes the engaging portion 8C (FIG. 14A).

The locking portion 37C is locked to the surface, on the top absorbent body 3C contacting side, of the base absorbent body 2C. That is, the surface on the top absorbent body 3C contacting side of the base absorbent body 2C is the engaging portion 8C. More specifically, a position where the locking portion 37C is locked (a base absorbent body side portion to be locked) is closer to an outer edge (the rear edge 230) in the longitudinal direction LD in relation to a position of the locking portion 37C in a case where the top absorbent body 3C and the base absorbent body 2C are placed in a substantially planar shape.

In the fourth embodiment, the top absorbing portion 30C includes the elastic member 82C, but is not limited thereto. The elastic member 82C may be arranged such that an end, on the side of the free end 31, of the elastic member 82C covers a portion of a handle portion 40. That is, the elastic member 82C may be arranged so as to straddle the vicinity, on the side of a top absorbing portion 30, of the handle portion 40 and the top absorbing portion 30 on a surface thereof on the base absorbent body 2C contacting side in the top absorbent body 3C.

2.4. Fifth Embodiment

As shown in FIGS. 15A and 15B, an absorbent article according to the fifth embodiment differs from that of the first embodiment in the forms of a locking portion 37D and a engaging portion (or a portion to be locked) 8D. FIG. 15A is an enlarged plan view, on the side of a rear edge 230, of a base absorbent body 2D according to the fifth embodiment. FIG. 15B is an enlarged back view, on the side of a free end 31, of a top absorbent body 3D according to the fifth embodiment.

The locking portion 37D according to the fifth embodiment is arranged in the base absorbent body 2D. More specifically, the locking portion 37D is preferably spaced, for example, 0 mm to 100 mm, and more preferably spaced 20 mm to 80 mm, apart from the rear edge 230 in the base absorbent body 2D. It is preferable for the locking portion 37D to be arranged so as to have a substantially vertically-long shape along a longitudinal direction LD of the base absorbent body 2D. In addition, the locking portion 37D may be arranged so as to cross a central portion 20 in a width direction WD.

An example of the length in the longitudinal direction LD of the locking portion 37D is 5 mm to 100 mm, and preferably 10 mm to 80 mm. In addition, an example of the length in the width direction WD of the locking portion 37D is 5 mm to 80 mm, and preferably 7.5 mm to 60 mm.

For example, the same member as that forming the locking portion 37 in the first embodiment can be used as the member that forms the locking portion 37D.

The engaging portion 8D is arranged in the top absorbent body 3D. In detail, the engaging portion 8D is arranged on the base absorbent body contacting side in a top absorbing portion 30D and in the vicinity of a free end portion 32. In more detail, the engaging portion 8D is arranged on the base absorbent body contacting side in the top absorbing portion 30D so as to cover a surface, on the side of the free end portion 32, of an absorbent core 35. In a case where the length thereof in the longitudinal direction LD is more than 15 cm, excreta that cannot be absorbed by the top absorbent body 3D can be inhibited from being transferred to the base absorbent body 2D.

It should be noted that, in the case of the fifth embodiment, the back sheet 34 arranged in the posterior region of the top absorbing portion 30 in the first embodiment need not be arranged.

An example of a member forming the engaging portion 8D, for example, is a loop material including a sheet having liquid impermeability. By forming the engaging portion 8D of a loop material that includes a sheet having liquid impermeability, the locking portion 37D can be locked when brought into contact with the engaging portion 8D and inhibits a liquid from oozing out of the base absorbent body 2C contacting side in the top absorbent body 3D.

When the position of the top absorbent body 3D is adjusted in the process of putting on, a portion on the side of the free end 31 of the top absorbent body 3D projects toward underwear. When in this state, it is possible to inhibit excreta absorbed from the base absorbent body contacting side in the top absorbent body 3D from oozing out toward the underwear.

The locking portion 37D serving as a base absorbent body side locking portion is arranged closer to an outer edge (the rear edge 230) in the longitudinal direction LD in relation to a position of the engaging portion 8D serving as a top absorbent body side portion to be locked in a case where the top absorbent body 3D and the base absorbent body 2D are formed in a substantially planar shape.

2.5. Sixth Embodiment

An absorbent article 1F according to the sixth embodiment differs from that of the first embodiment in the form of a handle portion 40F.

As shown in FIG. 16, the handle portion 40F has a handle portion top sheet 42F and a handle portion back sheet 43F having liquid impermeability, for example, formed on both surfaces thereof.

In the handle portion 40F, a top sheet 331 and a back sheet 34 in a top absorbing portion 30F are layered such that an end of a region formed of only the sheets is sandwiched between the handle portion top sheet 42F and the handle portion back sheet 43F and are compression-bonded by embossing. It is preferable for layers in an obtained layered composition to be bonded with hot melt adhesives.

The handle portion top sheet 42F is arranged on the skin contacting side in the handle portion 40F. A sheet having liquid impermeability and having concavities and convexities can be used for the handle portion top sheet 42F. When a smooth sheet such as a film having no concavities and convexities is used, the absorbent article 1F may give an uncomfortable feeling upon becoming moist when worn. A non-woven fabrics such as spunlace, spunbond, melt blown, needle punch, and through-air non-woven fabrics composed of hydrophobic fibers can be exemplified as the sheet material. An SMS non-woven fabric is preferable from the viewpoint of giving rigidity to the handle portion 40F.

The handle portion back sheet 43F is not particularly limited as a sheet material. The non-woven fabric and films taken as examples in the foregoing can be used. Preferably, a material that allows the handle portion 40F to have rigidity by being laminated to the handle portion top sheet 42F may be preferably used. The handle portion back sheet 43F is not an indispensable constituent element, and the handle portion 40F may be formed of only the handle portion top sheet 42F.

Furthermore, the handle portion top sheet 42F and the handle portion back sheet 43F can be subjected to embossing. The embossing allows rigidity to be imparted even if an SMS non-woven fabric is not used. In addition, forming concavities and convexities on respective top surfaces of the handle portion top sheet 42F and the handle portion back sheet 43F provides an indication for a user searching for the handle portion 40F by touch.

In addition, the handle portion top sheet 42F may include a locking portion 37F formed on the skin contacting side. The locking portion 37F is formed of a pressure sensitive adhesive, and can be mainly made to adhere to the wearer's body. In the present embodiment, the locking portion 37F, together with the locking portion 37, may be provided. Alternatively, only the locking portion 37F may be provided.

2.6. Seventh Embodiment

As shown in FIG. 17, an absorbent article 1J according to the seventh embodiment differs from that in the first embodiment in the form of a handle portion 40J. The handle portion 40J can be formed in a wave shape in a side portion thereof in a longitudinal direction LD. Forming the side portion in the longitudinal direction LD of the handle portion 40J in a wave shape allows cases where a corner portion comes into contact with the skin to produce an uncomfortable feeling to be reduced.

2.7. Eighth Embodiment

As shown in FIGS. 18 and 19, an absorbent article 1K according to an eighth embodiment differs from that of the first embodiment in that a top layer 33K in a top absorbent body 3K is composed of a top sheet 331 and a back sheet 34 and a handle portion 40K and the top absorbent body 3K are connected to each other by an elastic member 36K.

As shown in FIGS. 18 and 19, the elastic member 36K is connected to a free end portion 32 in a top absorbing portion 30K so as to project outward at an one end thereof while being connected to the handle portion 40K at the other end.

As shown in FIG. 18, in the surface layer 33K in the top absorbent body 3K, only the top sheet 331 is arranged on the skin contacting side in the top absorbent body 3K, and the back sheet 34 is entirely arranged on the base absorbent body 2 contacting side in the top absorbent body 3K. Then, the top sheet 331 and the back sheet 34 are fixed to each other by subjecting both side portions of the top absorbing portion 30K to embossing along a longitudinal direction LD.

Both ends in the longitudinal direction LD of the top absorbing portion 30K are regions having no absorbent core 28 and formed of only the top sheet 331 and the back sheet 34 on the side of the free end 31. Additionally, out of the two regions, the region on the side of a front edge 220 and the region on the side of a rear edge 230, in a case where the top absorbent body 3K is arranged on the base absorbent body 2, are a fixed portion 4 and the free end 31, respectively.

It is preferable for, in the elastic member 36K, a material having stretchability to be arranged in a range of 3% to 50% and preferably in a range of 5% to 20% of the length in the longitudinal direction LD from the fixing portion 4 (not shown) to a locking portion 37K in the top absorbent body 3K. Arranging such a material allows a feeling of pressure on the wearer's body to be reduced. In addition, a member exemplified by the engaging portion 8B in the third embodiment, for example, can be used as a member capable of forming the elastic member 36K.

At one end, on the side of the top absorbing portion 30K, of the elastic member 36K, the top sheet 331 and the back sheet 34 in the top absorbing portion 30 and the elastic member 36K are arranged to be layered such that the elastic member 36K is sandwiched between the top sheet 331 and the back sheet 34K, and are subjected to compression bonding, as shown in FIG. 22.

In addition, at the other end, on the side of the handle portion 40K of the elastic member 36K, the handle portion 40K and the elastic member 36K are subjected to compression bonding and are connected to each other. The handle portion 40K is formed of a handle portion top sheet 42K and a handle portion back sheet 43K. In detail, the handle portion back sheet 43K, the elastic member 36K, and the handle portion top sheet 42K are arranged to be layered in this order from below, for example, and a portion where all these are layered is subjected to compression bonding, to form the handle portion 40K. It should be noted that the handle portion top sheet 42K and handle portion back sheet 43K can be the same as the handle portion top sheet 42F and the handle portion back sheet 43F of the sixth embodiment, respectively.

Alternatively, in the present embodiment, although the elastic member 36K is relatively short in the longitudinal direction LD in the top absorbent body 3K, the length thereof may be greater than the length exemplified in the present embodiment. In a case where the elastic member 36K is relatively long, for example, it can be folded in a Z shape and accommodated below the top absorbent body 3K.

In the handle portion 40K, an indication sign 41K serving as a guiding element indicating a predetermined operation or the like can be arranged. More specifically, the indication sign 41K is arranged in a visible state. The indication sign 41K can be the same as the indication sign 41G of the eighth embodiment.

In addition, the indication sign 41K can be printed by preparing an indication sign sheet 44K serving as a guiding element sheet. The indication sign sheet 44K is a sheet for printing the indication sign 41K, and paper that has not been subjected to creping, a non-woven fabric whose surface has been subjected to embossing, and an SMS non-woven fabric on which polyethylene has been laminated can be exemplified as materials therefor.

It should be noted that the indication sign sheet 44K need not be arranged to respective tips in the longitudinal direction LD of the handle portion surface sheet 42K and the handle portion back sheet 43K. That is, a state where the indication sign sheet 44K is completely covered with the handle portion top sheet 42K and the handle portion back sheet 43K is preferable. When the indication sign sheet 44K is arranged to the tip, an edge at the tip becomes rigid, thereby potentially giving an uncomfortable feeling to the user.

The handle portion 40K is formed by arranging the handle portion back sheet 43K, the elastic member 36K, and the handle portion top sheet 42K to be layered in this order from below, and subjecting a portion where all these are layered to compression bonding. In a case where the handle portion 40K includes the indication sign sheet 44K, it is preferably arranged to be layered between the handle portion back sheet 43K and the elastic member 36K.

The locking portion 37K and/or the locking portion 37K' can be arranged in the handle portion 40K. The locking portion 37K can be arranged on the base absorbent body 2 contacting side in the handle portion 40K, and is locked to the base absorbent body 2. Alternatively, the locking portion 37K' can be arranged on the body contacting side in the handle portion 40K, and is locked to the skin of the user. In addition, the locking portion 37 according to the first embodiment, together with the locking portions 37K and 37K', may be arranged, and any one or two among the locking portions may be arranged.

A member used for the locking portions 37K and 37K' can be the same member as that of the first embodiment.

Connecting the top absorbing portion 30K and the handle portion 40K to each other with the elastic member 36K sandwiched therebetween allows the elastic member 36K to serve as a buffer portion. For example, even when the wearer's body or the underwear moves when the absorbent article 1K is worn, the elastic member 36K follows the movement to expand and contract, for example, which allows such an effect based on a predetermined manipulation according to the wearer's body that the locking portion 37K and/or the locking portion 37K' is/are unlocked because the underwear is pulled to be reduced.

In addition, although the locking portion 37K is arranged on the base absorbent body 2 contacting side in the handle portion 40K and is locked to the underwear when the absorbent article 1K is worn to position the top absorbent body 3K, as in the first embodiment, it may be folded toward the underwear contacting side in the base absorbent body 2 and locked to the underwear contacting side to position the top absorbent body 3K.

In the eighth embodiment, although the handle portion 40K includes the handle portion top sheet 42K, the handle portion back sheet 43K, and the indication sign sheet 44K, the present invention is not limited thereto. For example, the handle portion 40K may include only the handle portion top sheet 42K, and the indication sign 41K may be formed on a top surface of the handle portion top sheet 42K. Alternatively, the handle portion 40K need not include the indication sign 41K. Then, only the elastic member 36 and the handle portion top sheet 42K can be joined to each other.

In the above-mentioned embodiment, although the temporary fixing portions 5 are formed at the free end portion 32 in the vicinity of the handle portion 40 by dot-shaped (circular) embossing in the first embodiment, the present invention is not limited thereto. For example, a plurality of linear or dot-shaped embosses may be continuously formed along the longitudinal direction LD on both sides in the width direction WD in the top absorbing portion 30. The plurality of dot-shaped embosses may be formed on the entire surface of the top absorbing portion 30. Furthermore, the shape of the embosses is not limited to the dot shape, and the embosses may have any shape. Alternatively, a design such as a flower pattern may be provided, as in the embossing in the handle portion 40 of the first embodiment.

Although fibers in corresponding portions in the top absorbing portion 30 and the base absorbent body 2 are lightly thermally fused by dot-shaped embossed members in order to perform embossing, a processing method is not limited thereto. The corresponding portions where embossing is performed may be formed by pin embossing so as to penetrate the absorbent core 35 in the top absorbing portion 30 and the absorbent core 28 in the base absorbent body 2.

In addition, although in the abovementioned embodiments, the locking portion 37 arranged in the top absorbent body 3 as locking means for locking the base absorbent body 2 and the top absorbent body 3 and the top sheet 27 in the base absorbent body 2 as a portion to be locked is described, the present invention is not limited thereto. For example, the portion to be locked and the locking portion may be respectively arranged on the side of the top absorbent body 3 and the base absorbent body 2, as shown in the third embodiment and the fifth embodiment, for example. In addition, a sheet-shaped member may be arranged on the top surface of the base absorbent body 2 in the portion to be locked, as in the second embodiment. Furthermore, the sheet-shaped member may have stretchability. In a case where the portion to be locked is a sheet-shaped member having stretchability, it serves as a buffer region that prevents the locking portion 37 from coming off the portion to be locked because the portion to be locked is stretched when the wearer's body or the underwear moves. Furthermore, an elastic member may be arranged on the side of the locking portion 37, as in the third embodiment and the fourth embodiment. More specifically, an elastic member may be arranged between the base absorbent body 2 or the top absorbent body 3 and the locking portion 37.

In the abovementioned embodiments, although the locking portion 37 is locked to the base absorbent body 2 in a worn state, the present invention is not limited thereto, and may be locked to the inside of the underwear serving as a garment arranged outside the absorbent article. More specifically, the locking portion 37 is locked to an inner side surface of the underwear with the absorbent article 1 arranged between the wearer's body serving as a wearing object and the underwear serving as a garment arranged so as to cover the wearer's body. In this case, the locking portion 37 is arranged closer to the free end 31 in relation to the position where the locking portion 37 is arranged when locked to the base absorbent body 2.

In the abovementioned embodiments, although the base absorbent body 2 has the gathers 21A and 21B and the compressed grooves 22, the present invention is not limited thereto, and need not have the gathers 21A and 21B and the compressed grooves 22. In addition, although the base absorbent body 2 has the six compressed grooves 22 substantially equally spaced in the width direction WD in the central portion 20, the present invention is not limited thereto. For example, the base absorbent body 2 may include an annular compressed groove extending in the longitudinal direction LD and formed such that a portion, corresponding to the width direction WD, of the position Z is concaved inward in the width direction WD and a gently curved compressed groove formed outside a portion formed so as to be concaved inward in the width direction WD in the annular compressed groove.

In addition, in the embodiments, although the absorbent core 28 in the base absorbent body 2 includes the hollow portions 351 and 352 and the regions 353, 354, 355, 356, and 357 respectively having different basis weights, the respective positions where they are formed and the basis weights thereof are not limited thereto, and may be formed at other positions and may have different basis weights. In addition, the absorbent core 28 may have a uniform basis weight in all the regions.

In addition, in the present embodiment, although the temporary fixing portions 5 are contact-bonded to the base absorbent body 2 by embossing, the present invention is not limited thereto. For example, the temporary fixing portions 5 may be formed of olefin-based hot melt adhesives of low tackiness and an ultrasonic seal, for example.

In addition, the base absorbent body 2 is not limited to the abovementioned configuration thereof, and a sanitary napkin commercially available may be generally used. The overall shape of the base absorbent body 2 is not limited to a substantially rectangular shape and, for example, may be a vertically-long shape such as an elliptical shape.

3. Example

Test samples of the handle portion 40 were respectively produced in configurations shown in Table, described below, to perform sensory evaluations of hardness (flexural rigidity), flexure recovery, and a feeling of holding each of the test samples.

The hardness (flexural rigidity), the flexure recovery, and the holding feeling were evaluated by 10 women performing a sensory test. The test samples were tested in random order. The evaluation was the average of scores in a case where each of the items was evaluated on a scale of one to ten. The evaluation was represented by a double circle, a circle, a triangle, and a cross mark for an average scores of not less than eight, less than 8 to not less than 6, less than six to not less than four, and not more than four, respectively.

Evaluating Method

In a method for evaluating hardness, hardness that was preferable in gripping the handle portion 40 serving as a test sample was given a score.

Regarding the flexure recovery, the handle portion 40 serving as a test sample was folded into two and was left as it was for one hour under a temperature of 20° C. and a humidity of 60% with a load of 20 g/m² applied. Thereafter, after the handle portion 40 was left as it was for one hour with the load released and further under the same humidity, such hardness that did not produce an uncomfortable feeling at an end of a fold was scored.

The holding feeling of the handle portion 40 was evaluated with regards to the thickness of the handle portion 40. More specifically, the holding feeling in gripping the handle portion 40 was given a score depending on whether or not the holding feeling was a preferable thickness. "HMA" described in Table 1, described below, is an abbreviation of hot melt adhesives.

TABLE 1

| Test sample | Hardness B | Sensory | Recovery 2HB | Sensory | Thickness: Feeling of holding Thickness | Sensory | Configuration |
|---|---|---|---|---|---|---|---|
| 1 | 0.049 | X | 0.0961 | ⊚ | 0.912 | ○ | A through-air non-woven fabric having a basis weight of 35 g/m² |
| 2 | 0.1943 | ○ | 0.439 | ⊚ | 1.78 | ⊚ | Two through-air non-woven fabrics having a basis weight of 35 g/m² laminated with HMA |
| 3 | 0.3321 | ⊚ | 0.765 | ⊚ | 3.56 | ○ | Four through-air non-woven fabrics having a basis weight of 35 g/m² laminated with HMA |
| 4 | 0.3565 | ⊚ | 1.0248 | ⊚ | 1.75 | ⊚ | A through-air non-woven fabric having a basis weight of 35 g/m² and a film having a basis weight of 23 g/m² laminated with HMA and folded into three |
| 5 | 0.4507 | ⊚ | 0.5643 | ⊚ | 0.487 | Δ | Two SMS non-woven fabrics having a basis weight of 35 g/m² laminated with HMA |
| 6 | 0.5685 | ⊚ | 1.0863 | ⊚ | 0.741 | ○ | Three SMS non-woven fabrics having a basis weight of 35 g/m² laminated with HMA |
| 7 | 0.7795 | ⊚ | 2.914 | ⊚ | 0.906 | ⊚ | Four SMS non-woven fabrics having a basis weight of 35 g/m² laminated with HMA |
| 8 | 1.0865 | ○ | 6.3762 | ○ | 1.367 | ⊚ | Six SMS non-woven fabrics having a basis weight of 35 g/m² laminated with HMA |
| 9 | 1.2719 | Δ | 10.7168 | X | 1.567 | ⊚ | Seven non-woven fabrics having a basis weight of 35 g/m² laminated with HMA |

The results were that the hardness of the handle portion was preferably in a range of 0.1 to 1.2 ($10^{-4}$ N·m²/m). In addition, the results were that the flexure recovery of the handle portion 40 was not more than 10 ($10^{-2}$ N·m/m). Furthermore, the results were that the thickness of the handle portion 40 was preferably in a range of 0.5 to 4 mm.

The invention claimed is:

1. An absorbent article comprising:
a first absorbent body having a longitudinal direction;
a second absorbent body arranged along the longitudinal direction on a skin contacting side of the first absorbent body;
a permanent fixing portion that permanently fixes the first absorbent body and the second absorbent body at a first end of the second absorbent body, wherein the second absorbent body has a second end opposite to the first end in the longitudinal direction and free of permanent attachment to the first absorbent body; and
a locking portion that is arranged between the permanent fixing portion and the second end on a skin non-contacting side opposite to the skin contacting side and temporarily locks the first absorbent body and the second absorbent body,
wherein
the first absorbent article has
a front edge and a rear edge opposite to the front edge in the longitudinal direction, and
a first position adapted to be in contact with an excretion area of a wearer in use,
the first position being arranged closer to the front edge than the rear edge,
the fixing portion is between the first position and the front edge, and
the second absorbent body projects in the longitudinal direction outwardly from said front and rear edges of the first absorbent portion, respectively.

2. The absorbent article according to claim 1, wherein the locking portion is arranged on a side of the second end of the second absorbent body.

3. The absorbent article according to claim 1, wherein the first absorbent body comprises a central portion and a first absorbent body side surface sheet covering the central portion, and
the first absorbent body side surface sheet is formed of a non-woven fabric that is engageable with the locking portion.

4. The absorbent article according to claim 1, further comprising a handle portion at the second end in the second absorbent body.

5. The absorbent article according to claim 4, wherein flexural rigidity of the handle portion is 0.1 to 1.2 ($10^{-4}$ N·m²/m).

6. The absorbent article according to claim 4, wherein flexure recovery of the handle portion is no greater than 10 ($10^{-2}$ N·m²/m).

7. The absorbent article according to claim 4, wherein the second absorbent body including the handle portion is arranged substantially at a center of the first absorbent body in a width direction perpendicular to the longitudinal direction.

8. The absorbent article according to claim 1, wherein the locking portion includes a hook fastener having a plurality of pins directed to a predetermined direction.

9. The absorbent article according to claim 1, wherein a width of the second absorbent body in a width direction perpendicular to the longitudinal direction is substantially uniform in the longitudinal direction.

10. The absorbent article according to claim 1, wherein the second absorbent body has a compression bonded portion where the first absorbent body and the second absorbent body are compressed and bonded together, said compression bonded portion being opposite to the second end of the second absorbent body in the longitudinal direction.

11. The absorbent article according to claim 10, wherein the permanent fixing portion is between said compression bonded portion and the temporary fixing portion.

* * * * *